US011071769B2

(12) United States Patent
Heckler et al.

(10) Patent No.: US 11,071,769 B2
(45) Date of Patent: Jul. 27, 2021

(54) LIPO-GLYCOPEPTIDE CLEAVABLE DERIVATIVES AND USES THEREOF

(71) Applicant: Insmed Incorporated, Bridgewater, NJ (US)

(72) Inventors: Ryan Heckler, Bridgewater, NJ (US); Donna Konicek, Bridgewater, NJ (US); Adam Plaunt, Bridgewater, NJ (US); Vladimir Malinin, Bridgewater, NJ (US); Walter Perkins, Bridgewater, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 0 days.

(21) Appl. No.: 16/615,214

(22) PCT Filed: May 22, 2018

(86) PCT No.: PCT/US2018/033963
§ 371 (c)(1),
(2) Date: Nov. 20, 2019

(87) PCT Pub. No.: WO2018/217808
PCT Pub. Date: Nov. 29, 2018

(65) Prior Publication Data
US 2020/0155640 A1 May 21, 2020

Related U.S. Application Data

(60) Provisional application No. 62/509,378, filed on May 22, 2017, provisional application No. 62/518,280, filed on Jun. 12, 2017, provisional application No. 62/560,413, filed on Sep. 19, 2017.

(51) Int. Cl.
*A61K 38/14* (2006.01)
*A61P 31/04* (2006.01)
*A61K 9/00* (2006.01)

(52) U.S. Cl.
CPC .............. *A61K 38/14* (2013.01); *A61K 9/008* (2013.01); *A61K 9/0073* (2013.01); *A61K 9/0075* (2013.01); *A61P 31/04* (2018.01)

(58) Field of Classification Search
CPC .... A61K 38/14; A61K 9/0019; A61K 9/0075; A61K 9/0078; A61K 9/008; A61K 9/08; A61K 9/10; A61K 9/1617; A61K 9/19; A61K 47/54; A61K 9/0073; A61K 9/5123; A61K 9/5153; A61P 31/04; C07K 9/008

See application file for complete search history.

(56) References Cited

U.S. PATENT DOCUMENTS

| 4,995,385 A | 2/1991 | Valentini et al. |
| 5,673,686 A | 10/1997 | Villax et al. |
| 5,740,794 A | 4/1998 | Smith et al. |
| 5,785,049 A | 7/1998 | Smith et al. |
| 5,855,913 A | 1/1999 | Hanes et al. |
| 5,874,064 A | 2/1999 | Edwards et al. |
| 5,976,574 A | 11/1999 | Gordon |
| 5,985,248 A | 11/1999 | Gordon et al. |
| 6,001,336 A | 12/1999 | Gordon |
| 6,051,256 A | 4/2000 | Platz et al. |
| 6,077,543 A | 6/2000 | Gordon et al. |
| 6,392,012 B1 | 5/2002 | Judice et al. |
| 6,455,669 B1 | 9/2002 | Judice et al. |
| 7,160,984 B2 | 1/2007 | Lee et al. |
| 7,273,845 B2 | 9/2007 | Zhao et al. |
| 7,442,388 B2 | 10/2008 | Weers et al. |
| 9,572,774 B2 * | 2/2017 | Lord ..................... A61K 9/0075 |
| 10,124,066 B2 * | 11/2018 | Perkins .................. A61K 47/24 |
| 10,420,722 B2 * | 9/2019 | Lord ..................... A61K 9/1617 |
| 10,471,149 B2 * | 11/2019 | Perkins ................. A61K 31/685 |
| 10,561,608 B2 * | 2/2020 | Lord ..................... A61K 9/4866 |
| 2002/0022590 A1 | 2/2002 | Leadbetter et al. |
| 2004/0242505 A1 | 12/2004 | Kaniga |
| 2005/0113561 A1 | 5/2005 | Liu et al. |
| 2007/0134729 A1 * | 6/2007 | Christensen .......... C07C 233/78 435/7.1 |
| 2008/0160092 A1 | 7/2008 | Batycky et al. |
| 2009/0104257 A1 | 4/2009 | Li et al. |

(Continued)

FOREIGN PATENT DOCUMENTS

| CN | 105085636 | 11/2015 |
| WO | WO-9916419 A1 | 4/1999 |

(Continued)

OTHER PUBLICATIONS

Nicas et al. Activity of Glycopeptides against Vancomycin-Resistant Gram-Positive Bacteria. Antimicrobial Agents and Chemotherapy, Sep. 1989, vol. 33, No. 9, pp. 1477-1481. (Year: 1989).*
Copenheaver, Blaine R., "International Search Report," prepared for PCT/US2018/033963, as dated Sep. 12, 2018, four pages.
Krause, Kevin M., et al.; "In Vitro Activity of Telavancin against Resistant Gram-Positive Bacteria"; Antimicrobial Agents and Chemotherapy, vol. 52, No. 7; Jul. 2008; pp. 2647-2652.
Shaw, J.P., et al.; "Pharmacokinetics, Serum Inhibitory and Bactericidal Activity, and Safety of Telavancin in Healthy Subjects"; Antimicrobial Agents and Chemotherapy, vol. 49, No. 1; Jan. 2005; pp. 195-201.

(Continued)

*Primary Examiner* — Marcela M Cordero Garcia
(74) *Attorney, Agent, or Firm* — Winstead PC

(57) ABSTRACT

The present invention provides certain lipo-glycopeptide cleavable derivatives and methods for using the same for the treatment of bacterial infections, for example, pulmonary bacterial infections. The LGPC derivatives include a cleavable moiety that in certain embodiments, is designed to allow for cellular uptake and/or a more rapid clearance of the glycopeptide metabolite (i.e., the cleaved glycopeptide) from the site of administration (e.g., the lung) as compared to the uncleaved LGPC.

20 Claims, 6 Drawing Sheets

(56) References Cited

U.S. PATENT DOCUMENTS

| | | | |
|---|---|---|---|
| 2011/0015119 A1* | 1/2011 | Chu | A61P 31/00 |
| | | | 514/3.1 |
| 2014/0079777 A1* | 3/2014 | Lord | A61K 9/1623 |
| | | | 424/451 |
| 2015/0314002 A1 | 11/2015 | Perkins et al. | |
| 2016/0089330 A1* | 3/2016 | Lord | A61K 38/14 |
| | | | 424/451 |
| 2016/0272682 A1 | 9/2016 | Boger | |
| 2017/0152291 A1 | 6/2017 | Boger | |
| 2017/0204138 A1* | 7/2017 | Cooper | C07K 5/06086 |
| 2019/0380955 A1* | 12/2019 | Lord | A61K 9/1623 |
| 2020/0155451 A1* | 5/2020 | Lord | A61K 9/1623 |
| 2020/0368312 A1* | 11/2020 | Heckler | A61K 9/0075 |

FOREIGN PATENT DOCUMENTS

| | | |
|---|---|---|
| WO | WO-9916420 A1 | 4/1999 |
| WO | WO-0021594 A2 | 4/2000 |
| WO | WO-0072904 A1 | 12/2000 |
| WO | WO-0100263 A2 | 1/2001 |
| WO | WO-2009042187 A1 | 4/2009 |
| WO | WO-2014085526 A1 | 6/2014 |
| WO | WO-2016007855 A1 | 1/2016 |
| WO | WO-2018081797 A1 | 5/2018 |
| WO | WO-2018217800 A1 | 11/2018 |

OTHER PUBLICATIONS

Mendes, Rodrigo E., et al.; "Telavancin in Vitro Activity against a Collection of Methicillin-Resistant *Staphylococcus aureus* Isolates, Including Resistant Subsets, from the United States"; Antimicrobial Agents and Chemotherapy, vol. 59, No. 3; Mar. 2015; pp. 1811-1814.

Goss, Christopher H., et al.; "Review: *Staphylococcus aureus* and MRSA in cystic fibrosis"; Journal of Cystic Fibrosis, vol. 10; Jun. 29, 2011; pp. 298-306.

Nagarajan, R., et al.; "Synthesis and Antibacterial Evaluation of N-Alkyl Vancomycins"; The Journal of Antibiotics, vol. 42, No. 1; Jan. 1989; pp. 63-72.

Soppimath, Kumaresh S., et al.; "Biodegradable polymeric nanoparticles as drug delivery devices"; Journal of Controlled Release 70 (2001); Feb. 2001; pp. 1-20.

Álvarez-Lerma, Francisco, et al.; "Gram-Positive Cocci Infections in Intensive Care"; Drugs 2006; 66 (6); Dec. 31, 2005; pp. 751-768.

Clinical and Laboratory Standards Institute (CLSI); "M07 Methods for Dilution Antimicrobial Susceptibility Tests for Bacteria That Grow Aerobically"; 11th ed.; Jan. 2018; 112 pages.

Yarlagadda, Venkateswarlu, et al.; "Membrane Active Vancomycin Analogues: A Strategy to Combat Bacterial Resistance" J. Med. Chem. 2014, 57; May 5, 2014; pp. 4558-4568.

"Glycopeptides Classification, Occurrence, and Discovery", by Raymond C. Rao and Louise W. Crandall, ("Drugs and the Pharmaceutical Sciences" vol. 63, edited by Ramakrishnan Nagarajan, published by Marcal Dekker, Inc. (cited on p. 16 of U.S. Appl. No. 62/509,378, p. 16 of U.S. Appl. No. 62/518,280 and p. 16 of U.S. Appl. No. 62/560,413).

de Jesús Valle, María Jose et al.; "Pulmonary versus Systemic Delivery of Antibiotics: Comparison of Vancomycin Dispositions in the Isolated Rat Lung"; Antimicrobial Agents and Chemotherapy; vol. 51 No. 10; Oct. 2007; pp. 3771-3774.

* cited by examiner

Vancomycin·HCl → Vancomycin–CH$_2$–R

DMF, DIPEA, 18 h, 25 °C;
MeOH, TFA, 2 h, 25 °C;
Borane tert-butylamine complex, 2 h, 25 °C;
Chromatography; Lyophilization DCM, THF, NaHCO$_3$,
Dess-Martin Periodinane
2h, RT

LIPO-GLYCOPEPTIDE CLEAVABLE DERIVATIVES AND USES THEREOF

CROSS REFERENCE TO RELATED APPLICATIONS

This application is a 371 national phase entry of PCT Application No. PCT/US2018/033963, filed May 22, 2018, which claims priority from U.S. Provisional Application Ser. No. 62/509,378, filed May 22, 2017; U.S. Provisional Application Ser. No. 62/518,280, filed Jun. 12, 2017; and U.S. Provisional Application Ser. No. 62/560,413, filed Sep. 19, 2017, the disclosures of each of which is incorporated by reference herein in their entireties.

BACKGROUND OF THE INVENTION

The high frequency of multidrug resistant bacteria, and in particular, Gram-positive bacteria, both in the hospital setting and the community present a significant challenge for the management of infections (Krause et al. (2008). Antimicrobial Agents and Chemotherapy 52(7), pp. 2647-2652, incorporated by reference herein in its entirety for all purposes).

The treatment of invasive *Staphylococcus aureus* (*S. aureus*) infections has relied significantly on vancomycin. However, the treatment and management of such infections is a therapeutic challenge because certain *S. aureus* isolates, and in particular, methicillin-resistant *S. aureus* isolates, have been shown to be resistant to vancomycin (Shaw et al. (2005). Antimicrobial Agents and Chemotherapy 49(1), pp. 195-201; Mendes et al. (2015). Antimicrobial Agents and Chemotherapy 59(3), pp. 1811-1814, each of which is incorporated by reference herein in its entirety for all purposes).

Because of the resistance displayed by many Gram-positive organisms to antibiotics, and the general lack of susceptibility to existing antibiotics, there is a need for new therapeutic strategies to combat infections due to these bacteria. The present invention addresses this and other needs.

SUMMARY OF THE INVENTION

In one aspect, the present invention addresses the need for new antibiotics and treatment methods by providing certain glycopeptides containing a primary amino conjugated lipophilic moiety that is cleavable by enzymatic hydrolysis, and methods for using the same. The lipophilic moiety is conjugated to the primary amino group via a functional group that can undergo enzymatic hydrolysis. Glycopeptides of the present invention are referred to herein in various embodiments, as lipo-glycopeptide cleavable (LGPC) derivatives. Without being bound by any particular theory or mechanism, it is believed that the cleavage of the lipophilic moiety promotes clearance of the glycopeptide from the site of administration. In one embodiment, the LGPC derivative clears more rapidly from the site of administration (e.g., the lung) as compared to a structurally similar glycopeptide having a non-cleavable lipophilic moiety conjugated to the counterpart primary amino group.

In one embodiment of a LGPC derivative, a compound of Formula (I), or a pharmaceutically acceptable salt thereof, is provided:

Glycopeptide-$R^1$ (I)

wherein,
$R^1$ is conjugated to the Glycopeptide at a primary amine group of the Glycopeptide;
$R^1$ is —$(CH_2)_{n1}$—C(O)—O—$(CH_2)_{n2}$—$CH_3$; —$(CH_2)_{n1}$—C(O)—NH—$(CH_2)_{n2}$—$CH_3$; —C(O)—$(CH_2)_{n2}$—$CH_3$; —$(CH_2)_{n1}$—NH—C(O)—$(CH_2)_{n2}$—$CH_3$; —$(CH_2)_{n1}$—O—C(O)—$(CH_2)_{n2}$—$CH_3$; —$(CH_2)_{n1}$—O—C(O)—NH—$(CH_2)_{n2}$—$CH_3$; —$(CH_2)_{n1}$—O—(CO)—O—$(CH_2)_{n2}$—$CH_3$ or —$(CH_2)_{n1}$—NH—C(O)—O—$(CH_2)_{n2}$—$CH_3$;
n1 is 1, 2, 3, 4 or 5; and
n2 is 6, 7, 8, 9, 10, 11, 12, 13, 14 or 15.

In one embodiment of a compound of Formula (I), or a pharmaceutically acceptable salt thereof, the Glycopeptide is vancomycin, telavancin, chloroeremomycin or decaplanin. In a further embodiment, the Glycopeptide is telavancin, chloroeremomycin or decaplanin.

In one embodiment of a compound of Formula (I), or a pharmaceutically acceptable salt thereof, $R_1$ is —$(CH_2)_{n1}$—C(O)—NH—$(CH_2)_{n2}$—$CH_3$; —$(CH_2)_{n1}$—NH—C(O)—$(CH_2)_{n2}$—$CH_3$ or —$(CH_2)_{n1}$—O—C(O)—$(CH_2)_{n2}$—$CH_3$; n1 is 1 or 2, and n2 is 6, 7, 8, 9, 10, 11, 12, 13, 14 or 15. In a further embodiment, the Glycopeptide is vancomycin. In an even further embodiment, n2 is 6, 7, 8, 9, 10, 11, 12, or 14.

In one embodiment of a compound of Formula (I), or a pharmaceutically acceptable salt thereof, $R_1$ is —$(CH_2)_{n1}$—NH—C(O)—$(CH_2)_{n2}$—$CH_3$ or —$(CH_2)_{n1}$—O—C(O)—$(CH_2)_{n2}$—$CH_3$; n1 is 1, 2, 3 or 4, and n2 is 9, 10 or 11. In even a further embodiment, the Glycopeptide is vancomycin.

In one embodiment of a compound of Formula (I), or a pharmaceutically acceptable salt thereof, $R_1$ is —$(CH_2)_{n1}$—NH—C(O)—$(CH_2)_{n2}$—$CH_3$; n1 is 1, 2, 3 or 4, n2 is 9, 10 or 11. In even a further embodiment, the Glycopeptide is vancomycin.

In one embodiment of a compound of Formula (I), or a pharmaceutically acceptable salt thereof, $R_1$ is —$(CH_2)_{n1}$—O—C(O)—$(CH_2)_{n2}$—$CH_3$; n1 is 1, 2, 3 or 4, and n2 is 9, 10 or 11. In a further embodiment, the Glycopeptide is vancomycin. In a further embodiment, n1 is 2 and n2 is 10.

In one embodiment, a compound of the disclosure is represented by Formula (II), or a pharmaceutically acceptable salt thereof:

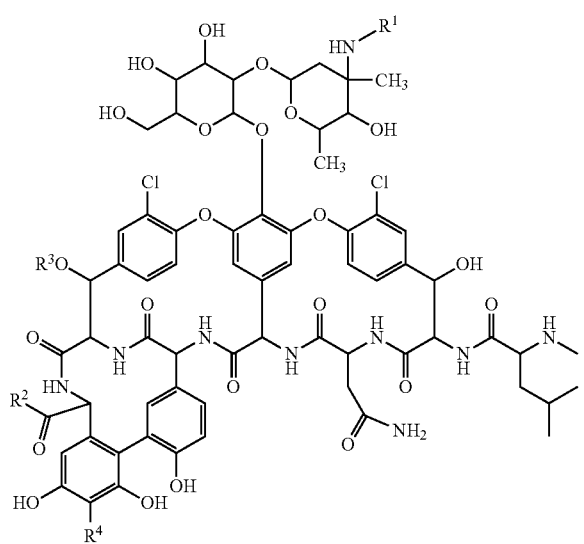

(II)

wherein, $R^1$ is —$(CH_2)_{n1}$—C(O)—O—$(CH_2)_{n2}$—$CH_3$; —$(CH_2)_{n1}$—C(O)—NH—$(CH_2)_{n2}$—$CH_3$; —C(O)—$(CH_2)_{n2}$—$CH_3$; —$(CH_2)_{n1}$—NH—C(O)—$(CH_2)_{n2}$—$CH_3$; —$(CH_2)_{n1}$—O—C(O)—$(CH_2)_{n2}$—$CH_3$; —$(CH_2)_{n1}$—O—C(O)—NH—$(CH_2)_{n2}$—$CH_3$; —$(CH_2)_{n1}$—O—(CO)—O—$(CH_2)_{n2}$—$CH_3$ or —$(CH_2)_{n1}$—NH—C(O)—O—$(CH_2)_{n2}$—$CH_3$;

n1 is 1, 2, 3, 4 or 5;
n2 is 6, 7, 8, 9, 10, 11, 12, 13, 14 or 15.
$R^2$ is OH or NH—$(CH_2)_q$—$R^5$;
q is 1, 2, 3, 4, or 5;
$R^3$ is

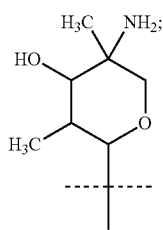

$R^4$ is H or $CH_2$—NH—$CH_2$—$PO_3H_2$; and
$R^5$ is —$N(CH_3)_2$, —$N^+(CH_3)_3$, —$N^+(CH_3)_2(n$-$C_{14}H_{29})$, or

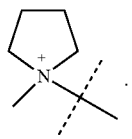

In one embodiment of a compound of Formula (II), or a pharmaceutically acceptable salt thereof, $R_1$ is —$(CH_2)_{n1}$—C(O)—NH—$(CH_2)_{n2}$—$CH_3$; —$(CH_2)_{n1}$—NH—C(O)—$(CH_2)_{n2}$—$CH_3$ or —$(CH_2)_{n1}$—O—C(O)—$(CH_2)_{n2}$—$CH_3$; n1 is 1 or 2, and n2 is 6, 7, 8, 9, 10, 11, 12, 13, 14 or 15. In a further embodiment, $R^2$ is OH or NH—$(CH_2)_3$—N$(CH_3)_2$.; and $R^3$ is H. In a further embodiment, n2 is 6, 7, 8, 9, 10, 11, 12, or 14.

In one embodiment of a compound of Formula (II), or a pharmaceutically acceptable salt thereof, $R_1$ is —$(CH_2)_{n1}$—NH—C(O)—$(CH_2)_{n2}$—$CH_3$ or —$(CH_2)_{n1}$—O—C(O)—$(CH_2)_{n2}$—$CH_3$. In a further embodiment, n1 is 1, 2, 3 or 4, and n2 is 9, 10 or 11. In even a further embodiment, n1 is 2 and n2 is 10. In still even a further embodiment, $R^2$ is OH, $R^3$ is H and $R^4$ is H.

In one embodiment of a compound of Formula (II), or a pharmaceutically acceptable salt thereof, $R_1$ is —$(CH_2)_{n1}$—NH—C(O)—$(CH_2)_{n2}$—$CH_3$. In a further embodiment, n1 is 1, 2, 3 or 4, and n2 is 9, 10 or 11. In even a further embodiment, n1 is 2 and n2 is 10. In still even a further embodiment, $R^2$ is OH, $R^3$ is H and $R^4$ is H.

In one embodiment of a compound of Formula (II), or a pharmaceutically acceptable salt thereof, $R_1$ is —$(CH_2)_{n1}$—O—C(O)—$(CH_2)_{n2}$—$CH_3$. In a further embodiment, n1 is 1, 2, 3 or 4, and n2 is 9, 10 or 11. In even a further embodiment, n1 is 2 and n2 is 10. In still even a further embodiment, $R^2$ is OH, $R^3$ is H and $R^4$ is H.

In one embodiment of a compound of Formula (II), or a pharmaceutically acceptable salt thereof, $R_1$ is —$(CH_2)_{n1}$—C(O)O—$(CH_2)_{n2}$—$CH_3$ or —$(CH_2)_{n1}$—C(O)NH—$(CH_2)_{n2}$—$CH_3$. In a further embodiment, n1 is 1, 2, 3 or 4, and n2 is 9, 10 or 11. In even a further embodiment, n1 is 2 and n2 is 10. In still even a further embodiment, $R^2$ is OH, $R^3$ is H and $R^4$ is H.

In one embodiment of a compound of Formula (II), or a pharmaceutically acceptable salt thereof, $R_1$ is —C(O)—$(CH_2)_{n2}$—$CH_3$. In a further embodiment, n2 is 9, 10 or 11. In even a further embodiment, n1 is 2 and n2 is 10. In even a further embodiment, $R^2$ is OH, $R^3$ is H and $R^4$ is H.

In another embodiment of a compound of Formula (II), or a pharmaceutically acceptable salt thereof, $R_2$ is —NH—$(CH_2)_q$—$R_3$. In a further embodiment, q is 3 and $R_3$ is —$N(CH_3)_2$. In even a further embodiment, n1 is 1, 2, 3 or 4 and n2 is 9, 10 or 11. In still even a further embodiment, $R^3$ is H and $R^4$ is H. In even a further embodiment, $R^1$ includes an amide group.

In another embodiment of a compound of Formula (II), or a pharmaceutically acceptable salt thereof, $R_2$ is —NH—$(CH_2)_q$—$R_3$. In a further embodiment, q is 3 and $R_3$ is —$N(CH_3)_2$. In even a further embodiment, n1 is 1, 2, 3 or 4 and n2 is 9, 10 or 11. In still even a further embodiment, $R^3$ is H and $R^4$ is H. In even a further embodiment, $R^1$ includes an ester group. In another embodiment of a compound of Formula (II), or a pharmaceutically acceptable salt thereof, n1 is 1, 2, 3 or 4, and n2 is 9, 10 or 11. In even a further embodiment, n1 is 2 and n2 is 10. In still even a further embodiment, $R^2$ is OH, $R^3$ is

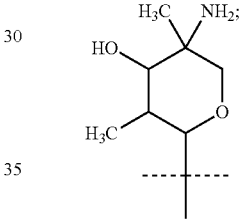

and $R^4$ is H.

In one embodiment of a compound of Formula (II), or a pharmaceutically acceptable salt thereof, n1 is 1, 2, 3 or 4, n2 is 9, 10 or 11, and $R^4$ is $CH_2$—NH—$CH_2$—$PO_3H_2$. In a further embodiment, n1 is 2 and n2 is 10. In even a further embodiment, $R^2$ is OH and $R^3$ is H.

In yet another aspect of the invention, a composition is provided comprising an effective amount of a compound of Formula (I), Formula (II), or a pharmaceutically acceptable salt of one of the foregoing. In a further embodiment, the composition is a dry powder.

In one embodiment, the composition provided herein comprises a plurality of nanoparticles of the compound of Formula (I) or (II), or a pharmaceutically acceptable salt thereof, in association with a polymer. In further embodiments, the compositions are suitable for administration via the pulmonary route, e.g., via inhalation with a nebulizer, a dry powder inhaler or a metered dose inhaler.

In yet another aspect of the invention, a method is provided for treating a bacterial infection in a patient in need thereof. The bacterial infection can comprise planktonic bacteria and/or bacteria present in a biofilm. The method comprises administering to the patient in need of treatment, a composition comprising a therapeutically effective amount of a compound of Formula (I), Formula (II), or a pharmaceutically acceptable salt of a compound of Formula (I) or (II). In one embodiment, the bacterial infection is a gram positive bacterial infection. In a further embodiment, the bacterial infection is a pulmonary bacterial infection. As such, in one embodiment, the administering is via the pulmonary route, e.g., via dry powder inhaler.

In another embodiment, the administering is via the intravenous (IV) route for the treatment of a localized bacterial infection. In one embodiment, the compound administered to the patient is a compound of Formula (II) wherein n1 is 2, 3 or 4, and n2 is 9, 10 or 11. In a further embodiment, $R^1$ includes an ester moiety. In even a further embodiment, n1 is 2 and n2 is 10. In still even a further embodiment, $R^2$ is OH, $R^3$ is H and $R^4$ is H.

In one embodiment, the bacterial infection is an infection caused by a Gram-positive microorganism. In one embodiment, the bacterial infection is a pulmonary bacterial infection. In a further embodiment, the pulmonary bacterial infection is a Gram-positive cocci infection. In even a further embodiment, the pulmonary bacterial infection is a *Staphylococcus, Enterococcus* or *Streptococcus* infection. In even a further embodiment, the administering comprises administering via inhalation.

*Streptococcus pneumoniae* is treated, in one embodiment, in a patient that has been diagnosed with community-acquired pneumonia, hospital-acquired pneumonia or purulent meningitis. An *Enterococcus* infection is treated, in one embodiment, in a patient that has been diagnosed with a urinary-catheter related infection. A *Staphylococcus* infection, e.g., *S. aureus* is treated in one embodiment, in a patient that has been diagnosed with mechanical ventilation-associated pneumonia.

In one embodiment of the present methods, a *Staphylococcus* infection is treated and is a *Staphylococcus aureus* (*S. aureus*) infection. In another embodiment, the *S. aureus* infection is a methicillin-resistant *S. aureus* (MRSA) infection.

In one embodiment of the present methods, an *Enterococcus* infection is treated and is an *Enterococcus faecalis* (*E. faecalis*) infection. In another embodiment of the present methods, the *Enterococcus* infection is an *Enterococcus faecium* (*E. faecium*) infection.

DETAILED DESCRIPTION OF THE INVENTION

Figure 1:
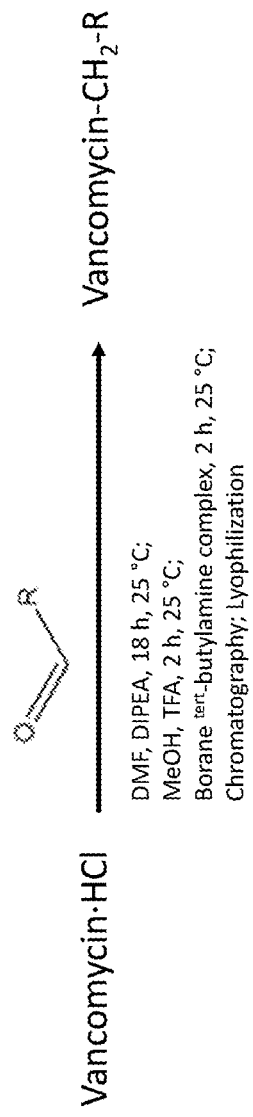
FIG. 1 shows the reductive amination of vancomycin to arrive at a LGPC derivative. The reaction occurs at the primary amine of vancomycin.
Figure 2:
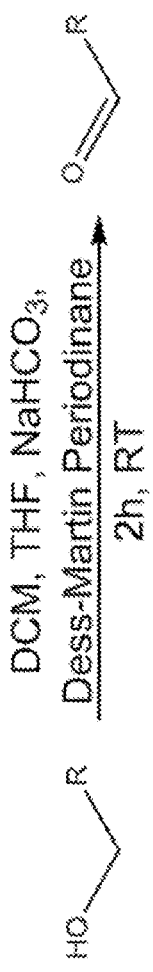
FIG. 2 shows one reaction scheme for aldehyde preparation.

The high frequency of multidrug resistant bacteria, and in particular, Gram-positive bacteria, both in the healthcare setting and the community present a significant challenge for the management of infections (Krause et al. (2008). *Antimicrobial Agents and Chemotherapy* 52(7), pp. 2647-2652, incorporated by reference herein in its entirety for all purposes). Moreover, methicillin resistant *S. aureus* (MRSA) infections in cystic fibrosis (CF) patients is a concern, and there is a lack of clinical data regarding approaches to eradicate such infections (Goss and Muhlebach (2011). *Journal of Cystic Fibrosis* 10, pp. 298-306, incorporated by reference herein in its entirety for all purposes).

Due to the high frequency of resistant pathogens, novel compounds and methods are needed to treat infections due to such pathogens. Moreover, it has been found that semi synthetic glycopeptides containing primary amino conjugated lipophilic moieties can accumulate in tissue and can exhibit long half-lives at the site of administration following administration (e.g., administration via inhalation). As such, glycopeptides that promote clearance from the site of administration are needed.

The present invention addresses the need for new antibiotics and treatment methods by providing certain glycopeptides containing a primary amino conjugated lipophilic moiety that is cleavable by enzymatic hydrolysis, and methods for using the same. The lipophilic moiety is conjugated to the primary amino group via a functional group that is capable of undergoing enzymatic hydrolysis. The functional group that undergoes enzymatic hydrolysis, in one embodiment, in conjugated to the primary amino group via a straight chain or branched alkyl group, e.g., a methyl, ethyl, propyl or butyl group. In another embodiment, the functional group is an amide that comprises the nitrogen atom from the primary amino group of the glycopeptide.

Glycopeptides of the present invention are referred to herein in various embodiments, as lipo-glycopeptide cleavable (LGPC) derivatives. Without being bound by any particular theory or mechanism, it is believed that the cleavage of the lipophilic moiety promotes clearance of the glycopeptide from the site of administration. In one embodiment, the LGPC derivative clears more rapidly from the site of administration (e.g., the lung) as compared to a structurally similar glycopeptide having a non-cleavable lipophilic moiety conjugated to the counterpart primary amino group.

As an example, in one embodiment, a glycopeptide containing a cleavable lipophilic group attached to a primary amino group of the glycopeptide clears from the site of administration at a faster rate than a glycopeptide having a non-cleavable lipophilic group attached to the same primary amino group. In another embodiment, the LGPC has a half-life ($T_{1/2}$) at the site of administration that is shorter than the $T_{1/2}$ of a glycopeptide having a non-cleavable lipophilic group attached to the primary amino group. The comparison of clearance is made in one embodiment, between glycopeptides having the same core structure, but for the different primary amino group conjugated moieties. One embodiment of an appropriate comparison is shown in Table A.

TABLE A

| LGPC derivative primary amino conjugated cleavable moiety | Semi-synthetic glycopeptide primary amino conjugated non-cleavable moiety |
|---|---|
| -(alkyl)$_{n1}$-Y$^1$-lipophilic group  vs. | -(alkyl)$_{n1}$-Y$^2$-lipophilic group |

Each n1 is the same for each comparison, or differs by 1, 2 or 3 carbon atoms.
Y$^1$ is a functional group that can undergo enzymatic hydrolysis, e.g., —O—C(O)—; —NH—C(O)—; —C(O)—O—; —C(O)—NH—; —O—C(O)—NH; NH—C(O)—O; O—C(O)—O
Y$^2$ is a functional group that cannot undergo enzymatic hydrolysis, e.g., —O—; —NH—; —S—S—; —SO$_2$—;
Alkyl is either substituted or unsubstituted.
Each lipophilic group is the same, or differs in length by one carbon or two carbon atoms.
The lipophilic group, in one embodiment, is an alkyl group, and can be straight chain or branched.
In a further embodiment, the alkyl group is substituted at one, two or three carbon atoms.

As such, in one embodiment, the LGPCs provided herein are intended to promote glycopeptide clearance from tissue, for example, increased clearance from the lung after local administration via inhalation. As cleavage of the delivered LGPC derivative occurs over a time T$_1$, an effective amount of LGPC derivative can remain at the site of action during T$_1$, or a portion thereof.

Cleavage, in one embodiment, is via an esterase. In another embodiment, cleavage occurs in vivo via an amidase. In another embodiment, cleavage occurs in vivo via a protease such as a peptidase.

Importantly, the compounds provided herein would not be considered prodrugs, even though they each contain a labile moiety. Rather, the uncleaved LGPCs provided herein are more active than their cleaved metabolite.

In one embodiment, the LGPC derivative provided herein has a shorter $T_{1/2}$ than a counterpart uncleavable lipophilic derivatized glycopeptide. In one embodiment, the $T_{1/2}$ of the LGPC is about 5-75% of the $T_{1/2}$ of the uncleavable lipophilic derivatized glycopeptide, including about 5-10%, 5-15%, 5-20%, 5-25%, 5-30%, 5-35%, 5-40%, 5-45%, 5-50%, 5-55%, 5-60%, 5-65%, 5-70%, 10-15%, 10-20%, 10-25%, 10-30%, 10-35%, 10-40%, 10-45%, 10-50%, 10-55%, 10-60%, 10-65%, 10-70%, 10-75%, 15-20%, 15-25%, 15-30%, 15-35%, 15-40%, 15-45%, 15-50%, 15-55%, 15-60%, 15-65%, 15-70%, 15-75%, 20-25%, 20-30%, 20-35%, 20-40%, 20-45%, 20-50%, 20-55%, 20-60%, 20-65%, 20-70%, 20-75%, 25-30%, 25-35%, 25-40%, 25-45%, 25-50%, 25-55%, 25-60%, 25-65%, 25-70%, 25-75%, 30-35%, 30-40%, 30-45%, 30-50%, 30-55%, 30-60%, 30-65%, 30-70%, 30-75%, 35-40%, 35-45%, 35-50%, 35-55%, 35-60%, 35-65%, 35-70%, 35-75%, 40-45%, 40-50%, 40-55%, 40-60%, 40-65%, 40-70%, 40-75%, 45-50%, 45-55%, 45-60%, 45-65%, 45-70%, 45-75%, 50-55%, 50-60%, 50-65%, 50-70%, 50-75%, 55-60%, 55-65%, 55-70%, 55-75%, 60-65%, 60-70%, 60-75%, 65-70%, 65-75%, or 70-75% of the $T_{1/2}$ of the uncleavable lipophilic derivatized glycopeptide.

In one embodiment, the LGPC derivative provided herein has a faster clearance rate from the site of administration than a counterpart uncleavable lipophilic derivatized glycopeptide. In one embodiment, the clearance rate of the LGPC is about 5-75% of the clearance rate of the uncleavable lipophilic derivatized glycopeptide, including about 5-10%, 5-15%, 5-20%, 5-25%, 5-30%, 5-35%, 5-40%, 5-45%, 5-50%, 5-55%, 5-60%, 5-65%, 5-70%, 10-15%, 10-20%, 10-25%, 10-30%, 10-35%, 10-40%, 10-45%, 10-50%, 10-55%, 10-60%, 10-65%, 10-70%, 10-75%, 15-20%, 15-25%, 15-30%, 15-35%, 15-40%, 15-45%, 15-50%, 15-55%, 15-60%, 15-65%, 15-70%, 15-75%, 20-25%, 20-30%, 20-35%, 20-40%, 20-45%, 20-50%, 20-55%, 20-60%, 20-65%, 20-70%, 20-75%, 25-30%, 25-35%, 25-40%, 25-45%, 25-50%, 25-55%, 25-60%, 25-65%, 25-70%, 25-75%, 30-35%, 30-40%, 30-45%, 30-50%, 30-55%, 30-60%, 30-65%, 30-70%, 30-75%, 35-40%, 35-45%, 35-50%, 35-55%, 35-60%, 35-65%, 35-70%, 35-75%, 40-45%, 40-50%, 40-55%, 40-60%, 40-65%, 40-70%, 40-75%, 45-50%, 45-55%, 45-60%, 45-65%, 45-70%, 45-75%, 50-55%, 50-60%, 50-65%, 50-70%, 50-75%, 55-60%, 55-65%, 55-70%, 55-75%, 60-65%, 60-70%, 60-75%, 65-70%, 65-75%, or 70-75% of the clearance rate of the uncleavable lipophilic derivatized glycopeptide.

In one embodiment, the LGPC derivative provided herein has a minimum inhibitory concentration (MIC) against a particular bacterium that is lower than its cleaved metabolite. In particular embodiments the MIC of the LGPC is about 5-75% of the MIC of the cleaved metabolite, including about 5-10%, 5-15%, 5-20%, 5-25%, 5-30%, 5-35%, 5-40%, 5-45%, 5-50%, 5-55%, 5-60%, 5-65%, 5-70%, 10-15%, 10-20%, 10-25%, 10-30%, 10-35%, 10-40%, 10-45%, 10-50%, 10-55%, 10-60%, 10-65%, 10-70%, 10-75%, 15-20%, 15-25%, 15-30%, 15-35%, 15-40%, 15-45%, 15-50%, 15-55%, 15-60%, 15-65%, 15-70%, 15-75%, 20-25%, 20-30%, 20-35%, 20-40%, 20-45%, 20-50%, 20-55%, 20-60%, 20-65%, 20-70%, 20-75%, 25-30%, 25-35%, 25-40%, 25-45%, 25-50%, 25-55%, 25-60%, 25-65%, 25-70%, 25-75%, 30-35%, 30-40%, 30-45%, 30-50%, 30-55%, 30-60%, 30-65%, 30-70%, 30-75%, 35-40%, 35-45%, 35-50%, 35-55%, 35-60%, 35-65%, 35-70%, 35-75%, 40-45%, 40-50%, 40-55%, 40-60%, 40-65%, 40-70%, 40-75%, 45-50%, 45-55%, 45-60%, 45-65%, 45-70%, 45-75%, 50-55%, 50-60%, 50-65%, 50-70%, 50-75%, 55-60%, 55-65%, 55-70%, 55-75%, 60-65%, 60-70%, 60-75%, 65-70%, 65-75%, or 70-75% of the MIC of the cleaved glycopeptide. In certain embodiments, the bacterium is a Gram-positive bacterium. In a further embodiment, the bacterium is methicillin-resistant *Staphylococcus aureus* (MRSA).

In the methods provided herein, the bacterial infection can comprise planktonic bacteria, bacterial biofilm, or a combination thereof.

One or more compounds provided herein, e.g., a LGPC of Formula (I) or (II), or a pharmaceutically acceptable salt thereof, is delivered to a patient in need of treatment of the bacterial infection. In one embodiment, the bacterial infection is a pulmonary bacterial infection and the composition is administered via the pulmonary route (e.g., inhalation).

"Pharmaceutically acceptable salt" includes both acid and base addition salts. A pharmaceutically acceptable addition salt refers to those salts which retain the biological effectiveness and properties of the free bases, which are not biologically or otherwise undesirable, and which are formed with inorganic acids such as, but are not limited to, hydrochloric acid (HCl), hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid (e.g., as lactate), lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, acetic acid (e.g., as acetate), tartaric acid, thiocyanic acid, p-toluenesulfonic acid, trifluoroacetic acid (TFA), undecylenic acid, and the like. In one embodiment, the pharmaceutically acceptable salt is HCl, TFA, lactate or acetate.

A pharmaceutically acceptable base addition salt retains the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Inorganic salts include the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, A-ethylpiperidine, polyamine resins and the like. Organic bases that can be used to form a pharmaceutically acceptable salt include isopropylamine, diethylamine, ethanolamine, trimethylamine, dicyclohexylamine, choline and caffeine.

In one aspect, the present invention relates to methods for treating bacterial infections, for example, Gram-positive bacterial infections, and diseases associated with the same. In one embodiment, the Gram-positive bacterial infection is a pulmonary infection. In one embodiment, the infection is a bacterial biofilm infection. The method, in one embodiment, comprises administering to a patient in need thereof, a composition comprising an effective amount of a compound of Formula (I) or Formula (II), or a pharmaceutically acceptable salt thereof. The composition can be administered by any route. In the case of a pulmonary infection, in one embodiment, the composition is administered via a nebulizer, dry powder inhaler or a metered dose inhaler.

In one aspect of the present invention, an LGPC derivative of Formula (I) or (II), or a pharmaceutically acceptable salt, is provided. The LGPC derivatives of the present invention include a biologically-labile moiety (e.g., amide, ester) that is conjugated to a glycopeptide via an amine group, e.g., a primary amine, on the glycopeptide. Upon administration, the biologically-labile moiety undergoes cleavage (e.g., via hydrolysis or enzymatic cleavage), providing one or more glycopeptide metabolites. In some embodiments, the metabolite provides a decreased residence time in the lungs compared to the unmetabolized compounds, thereby assisting in elimination of the therapeutic agent from the organ (e.g., lung in the case of pulmonary administration).

The compounds and formula described herein are set forth graphically without depicting stereochemistry. However, one of ordinary skill in the art will understand that the LGPC derivatives described herein each have a stereochemical configuration. In some embodiments, a stereoisomer (e.g., enantiomer, diastereomer) or a combination of stereoisomers of the respective LGPC derivative are provided.

In one embodiment, the present invention is directed to a compound of Formula (I), or a pharmaceutically acceptable salt thereof:

$$\text{Glycopeptide-R}^1 \qquad \qquad (I)$$

$R^1$ is conjugated to the Glycopeptide at a primary amine group of the Glycopeptide;

$R^1$ is —$(CH_2)_{n1}$—C(O)—O—$(CH_2)_{n2}$—$CH_3$; —$(CH_2)_{n1}$—C(O)—NH—$(CH_2)_{n2}$—$CH_3$; —C(O)—$(CH_2)_{n2}$—$CH_3$; —$(CH_2)_{n1}$—NH—C(O)—$(CH_2)_{n2}$—$CH_3$; —$(CH_2)_{n1}$—O—C(O)—$(CH_2)_{n2}$—$CH_3$; —$(CH_2)_{n1}$—O—C(O)—NH—$(CH_2)_{n2}$—$CH_3$; —$(CH_2)_{n1}$—O—(CO)—O—$(CH_2)_{n2}$—$CH_3$ or —$(CH_2)_{n1}$—NH—C(O)—O—$(CH_2)_{n2}$—$CH_3$;

n1 is 1, 2, 3, 4 or 5; and
n2 is 6, 7, 8, 9, 10, 11, 12, 13, 14 or 15.

In one embodiment of a compound of Formula (I), or a pharmaceutically acceptable salt thereof, the Glycopeptide is vancomycin, telavancin, chloroeremomycin or decaplanin. In a further embodiment, the Glycopeptide is telavancin, chloroeremomycin or decaplanin.

The structures of hundreds of natural and semisynthetic glycopeptides have been determined. These structures are highly related and fall within five structural subtypes, I-V, and the present invention is not limited to a particular subtype, so long as the glycopeptide includes a primary amine group to conjugate the $R^1$ group. Of the varying structural subtypes, type I structures contain aliphatic chains, whereas types II, III, and IV include aromatic side chains within these amino acids. Unlike types I and II, types III and IV contain an extra F-O-G ring system. Type IV compounds have, in addition, a long fatty-acid chain attached to the sugar moiety. Structures of type V, such as complestatin, chloropeptin I, and kistamincin A and B, contain the characteristic tryptophan moiety linked to the central amino acid.

In one embodiment, one of the glycopeptides described in PCT publication no. WO 2014/085526, the disclosure of which is incorporated by reference herein for all purposes, can be used as the glycopeptide set forth in Formula (I).

In one embodiment of Formula (I), the Glycopeptide is A477, A35512, A40926, A41030, A42867, A47934, A80407, A82846, A83850, A84575, AB-65, actaplanin, actinoidin, ardacin, avoparcin, azureomycin, chlorooriencicin chloropolysporin, chloroeremomycin, decaplanin, N-demethylvancomycin, eremomycin, galacardin, helvecardin A, helvecardin B, izupeptin, kibdelin, LL-AM374, mannopeptin, MM45289, MM47761, MM47766. MM55266, MM55270, OA-7653, orienticin, parvodicin, ristocetin, ristomycin, synmonicin, teicoplanin, telavancin, UK-68597, UK-69542, UK-72051, vancomycin, or a pharmaceutically acceptable salt of one of the foregoing.

In one embodiment of Formula (I), the Glycopeptide is vancomycin. In one embodiment of Formula (I), the Glycopeptide is telavancin. In one embodiment of Formula (I), the Glycopeptide is chloroeremomycin. In one embodiment of Formula (I), the Glycopeptide is decaplanin.

In one embodiment of a compound of Formula (I), or a pharmaceutically acceptable salt thereof, n1 is 2 or 3; and n2 is 8, 9, 10, 11 or 12. In even a further embodiment, n1 is 2 and n2 is 10. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—C(O)—O—$(CH_2)_{n2}$—$CH_3$. In a further embodiment, n1 is 1, 2 or 3; and n2 is 8, 9, 10, 11 or 12. In even a further embodiment, n1 is 2 and n2 is 10. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—C(O)—NH—$(CH_2)_{n2}$—$CH_3$. In a further embodiment, n1 is 2 or 3; and n2 is 8, 9, 10, 11 or 12. In even a further embodiment, n1 is 2 and n2 is 10. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—NH—C(O)—$(CH_2)_{n2}$—$CH_3$. In a further embodiment, n1 is 1, 2 or 3; and n2 is 8, 9, 10, 11 or 12. In even a further embodiment, n1 is 2 and n2 is 10. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—O—C(O)—$(CH_2)_{n2}$—$CH_3$. In a further embodiment, n1 is 2 or 3; and n2 is 8, 9, 10, 11 or 12. In even a further embodiment, n1 is 2 and n2 is 10. In a further embodiment, the Glycopeptide is vancomycin, telavancin or chloroeremomycin. In even a further embodiment, the Glycopeptide is vancomycin In one embodiment of a compound of Formula (I), or a pharmaceutically acceptable salt thereof, $R^1$ is —C(O)—$(CH_2)_{n2}$—$CH_3$. In a further embodiment, n2 is 8, 9, 10, 11 or 12. In even a further embodiment, n2 is 10. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, n1 is 1, 2 or 3; and n2 is 10, 11, 12 or 13. In even a further embodiment, n1 is 2 and n2 is 10 or 11. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—C(O)—O—$(CH_2)_{n2}$—$CH_3$. In a further embodiment, n1 is 1, 2 or 3; and n2 is 10, 11, 12 or 13. In even a further embodiment, n1 is 2 and n2 is 10 or 11. a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—C(O)—NH—$(CH_2)_{n2}$—$CH_3$. In a further embodiment, n1 is 2 or 3; and n2 is 10, 11, 12 or 13. In even a further embodiment, n1 is 2 and n2 is 10 or 11. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—NH—C(O)—$(CH_2)_{n2}$—$CH_3$. In a further embodiment, n1 is 1, 2 or 3; and n2 is 10, 11, 12 or 13. In even a further embodiment, n1 is 2 and n2 is 10 or 11. In a further embodiment, the Glycopeptide is vancomycin, telavancin or chloroeremomycin. In even a further embodiment, the Glycopeptide is vancomycin.

In one embodiment of a compound of Formula (I), or a pharmaceutically acceptable salt thereof, $R^1$ is —$(CH_2)_{n1}$—O—C(O)—$(CH_2)_{n2}$—$CH_3$. In a further embodiment, n1 is 1, 2 or 3; and n2 is 10, 11, 12 or 13. In even a further embodiment, n1 is 2 and n2 is 10 or 11. In a further embodiment, the Glycopeptide is vancomycin, telavancin or chloroeremomycin. In even a further embodiment, the Glycopeptide is vancomycin In one embodiment of a compound of Formula (I), or a pharmaceutically acceptable salt thereof, $R^1$ is —C(O)—$(CH_2)_{n2}$—$CH_3$. In a further embodiment, n2 is 10, 11, 12 or 13. In even a further embodiment, n2 is 10 or 11. In a further embodiment, the Glycopeptide is vancomycin, telavancin or chloroeremomycin. In even a further embodiment, the Glycopeptide is vancomycin.

In another embodiment, a compound of Formula (II), or a pharmaceutically acceptable salt thereof, is provided:

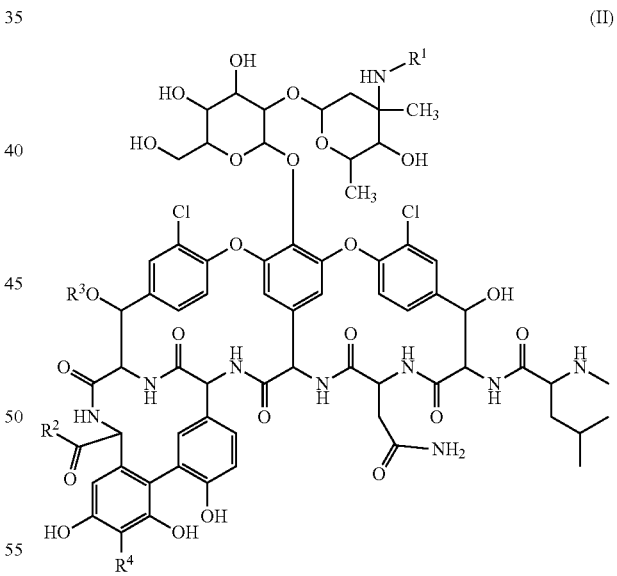

(II)

wherein,
$R^1$ is —$(CH_2)_{n1}$—C(O)—O—$(CH_2)_{n2}$—$CH_3$; —$(CH_2)_{n1}$—C(O)—NH—$(CH_2)_{n2}$—$CH_3$; —C(O)—$(CH_2)_{n2}$—$CH_3$; —$(CH_2)_{n1}$—NH—C(O)—$(CH_2)_{n2}$—$CH_3$; —$(CH_2)_{n1}$—O—C(O)—$(CH_2)_{n2}$—$CH_3$; —$(CH_2)_{n1}$—O—C(O)—NH—$(CH_2)_{n2}$—$CH_3$; —$(CH_2)_{n1}$—O—(CO)—O—$(CH_2)_{n2}$—$CH_3$ or —$(CH_2)_{n1}$—NH—C(O)—O—$(CH_2)_{n2}$—$CH_3$;
n1 is 1, 2, 3, 4 or 5;
n2 is 6, 7, 8, 9, 10, 11, 12, 13, 14 or 15;

$R^2$ is OH or NH—$(CH_2)_q$—$R^5$;
q is 1, 2, 3, 4, or 5;
$R^3$ is H or

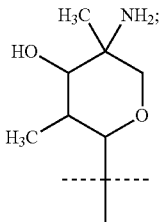

$R^4$ is H or $CH_2$—NH—$CH_2$—$PO_3H_2$; and
$R^5$ is —$N(CH_3)_2$, —$N^+(CH_3)_3$, —$N^+(CH_3)_2(n$-$C_{14}H_{29})$, or

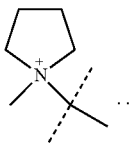

In some embodiments of Formula (II), $R^2$ is OH. In a further embodiment, $R^4$ is H.

In some embodiments of Formula (II), $R^2$ is OH. In a further embodiment, $R^4$ is $CH_2$—NH—$CH_2$—$PO_3H_2$.

In one embodiment of a compound of Formula (II), or a pharmaceutically acceptable salt thereof, $R^2$ is —NH—$(CH_2)_3$—$R^3$. In a further embodiment, $R^3$ and $R^4$ are H.

In one embodiment of a compound of Formula (II), or a pharmaceutically acceptable salt thereof, $R^2$ is —NH—$(CH_2)_3$—$R^3$. In a further embodiment, $R^4$ is $CH_2$—NH—$CH_2$—$PO_3H_2$.

In one embodiment of a compound of Formula (II), or a pharmaceutically acceptable salt thereof, $R^2$ is —NH—$(CH_2)_q$—$R^5$. In a further embodiment, $R^2$ is —NH—$(CH_2)_3$—$N(CH_3)_2$. In another embodiment, $R^2$ is —NH—$(CH_2)_3$—$N^+(CH_3)_3$. In yet other embodiments, $R^2$ is —NH—$(CH_2)_3$—$N^+(CH_3)_2(n$-$C_{14}H_{29})$. In a further embodiment, $R^2$ is

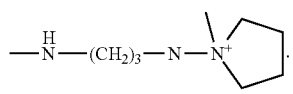

In one embodiment of a compound of Formula (II), or a pharmaceutically acceptable salt thereof, $R^2$ is —NH—$(CH_2)_q$—$N(CH_3)_2$. In another embodiment, $R^2$ is —NH—$(CH_2)_q$—$N^+(CH_3)_3$. In another embodiment, $R^2$ is —NH—$(CH_2)_q$—$R^5$ and $R^5$ is —$N^+(CH_3)_2(n$-$C_{14}H_{29})$. In yet another embodiment, $R^2$ is —NH—$(CH_2)_q$—$R^5$ and $R^5$

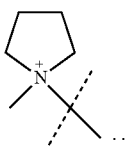

In one embodiment of a compound of Formula (II), or a pharmaceutically acceptable salt thereof, $R^1$ is —$(CH_2)_{n1}$—O—C(O)—$(CH_2)_{n2}$—$CH_3$ or —$(CH_2)_{n1}$—NH—C(O)—$(CH_2)_{n2}$—$CH_3$. In a further embodiment, $R^2$ is OH, $R^3$ is H and $R^4$ is H. In even a further embodiment, n1 is 1, 2 or 3, n2 is 9, 10, 11, 12, 13 or 14. In even a further embodiment, n1 is 2 and n2 is 10. In yet even a further embodiment, $R^1$ is —$(CH_2)_{n1}$—O—C(O)—$(CH_2)_{n2}$—$CH_3$.

In one embodiment of a compound of Formula (II), or a pharmaceutically acceptable salt thereof, $R^1$ is —$(CH_2)_{n1}$—NH—C(O)—$(CH_2)_{n2}$—$CH_3$. In a further embodiment, $R^2$ is OH, $R^3$ is H and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —$(CH_2)_{n1}$—O—C(O)—$(CH_2)_{n2}$—$CH_3$. In a further embodiment, $R^2$ is OH, $R^3$ is H and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —$(CH_2)_{n1}$—C(O)—O—$(CH_2)_{n2}$—$CH_3$. In a further embodiment, $R^2$ is OH, $R^3$ is H and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —$(CH_2)_{n1}$—C(O)—NH—$(CH_2)_{n2}$—$CH_3$. In a further embodiment, $R^2$ is OH, $R^3$ is H and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —C(O)—$(CH_2)_{n2}$—$CH_3$. In a further embodiment, $R^2$ is OH and $R^3$ and $R^4$ are H. In a further embodiment, n2 is 9, 10, 11, 12, 13 or 14. In even a further embodiment, n2 is 10.

In one embodiment of a compound of Formula (II), or a pharmaceutically acceptable salt thereof, $R^1$ is —$(CH_2)_{n1}$—O—C(O)—$(CH_2)_{n2}$—$CH_3$ or —$(CH_2)_{n1}$—NH—C(O)—$(CH_2)_{n2}$—$CH_3$. In a further embodiment, $R^2$ is OH, $R^3$ is

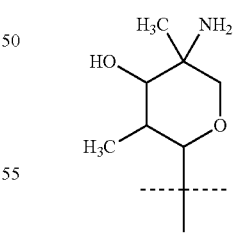

and $R^4$ is H. In even a further embodiment, n1 is 1, 2 or 3, n2 is 10, 11, 12, 13 or 14. In even a further embodiment, n1 is 2 and n2 is 10. In yet even a further embodiment, $R^1$ is —$(CH_2)_{n1}$—O—C(O)—$(CH_2)_{n2}$—$CH_3$.

In one embodiment of a compound of Formula (II), or a pharmaceutically acceptable salt thereof, $R^1$ is —$(CH_2)_{n1}$—NH—C(O)—$(CH_2)_{n2}$—$CH_3$. In a further embodiment, $R^2$ is OH, $R^3$ is

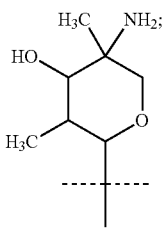

and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —(CH$_2$)$_{n1}$—O—C(O)—(CH$_2$)$_{n2}$—CH$_3$. In a further embodiment, $R^2$ is OH, $R^3$ is

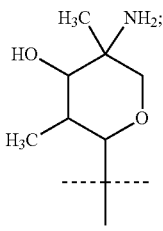

and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —(CH$_2$)$_{n1}$—C(O)—O—(CH$_2$)$_{n2}$—CH$_3$. In a further embodiment, $R^2$ is OH, $R^3$ is

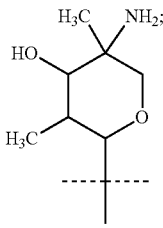

and $R^4$ is H. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —(CH$_2$)$_{n1}$—C(O)—NH—(CH$_2$)$_{n2}$—CH$_3$. In a further embodiment, $R^2$ is OH, $R^3$ is

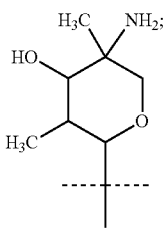

and $R^4$ is H. In even a further embodiment, n1 is 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —C(O)—(CH$_2$)$_{n2}$—CH$_3$. In a further embodiment, $R^2$ is OH, $R^3$ is

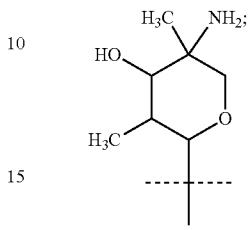

and $R^4$ is H. In even a further embodiment, n2 is 9, 10, 11, 12, 13 or 14. In even a further embodiment, n2 is 10.

In one embodiment of a compound of Formula (II), or a pharmaceutically acceptable salt thereof, $R^1$ is —(CH$_2$)$_{n1}$—O—C(O)—(CH$_2$)$_{n2}$—CH$_3$ or —(CH$_2$)$_{n1}$—NH—C(O)—(CH$_2$)$_{n2}$—CH$_3$. In a further embodiment, $R^2$ is OH, $R^3$ is H and $R^4$ is CH$_2$—NH—CH$_2$—PO$_3$H$_2$. In even a further embodiment, n1 is 1, 2 or 3, n2 is 9, 10, 11, 12, 13 or 14. In even a further embodiment, n1 is 2 and n2 is 10. In yet even a further embodiment, $R^1$ is —(CH$_2$)$_{n1}$—O—C(O)—(CH$_2$)$_{n2}$—CH$_3$.

In one embodiment of a compound of Formula (II), or a pharmaceutically acceptable salt thereof, $R^1$ is —(CH$_2$)$_{n1}$—NH—C(O)—(CH$_2$)$_{n2}$—CH$_3$. In a further embodiment. $R^2$ is OH, $R^3$ is H and $R^4$ is CH$_2$—NH—CH$_2$—PO$_3$H$_2$. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —(CH$_2$)$_{n1}$—O—C(O)—(CH$_2$)$_{n2}$—CH$_3$. In a further embodiment, $R^2$ is OH, $R^3$ is H and $R^4$ is CH$_2$—NH—CH$_2$—PO$_3$H$_2$. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —(CH$_2$)$_{n1}$—C(O)—O—(CH$_2$)$_{n2}$—CH$_3$. In a further embodiment, $R^2$ is OH, $R^3$ is H and $R^4$ is CH$_2$—NH—CH$_2$—PO$_3$H$_2$. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —(CH$_2$)$_{n1}$—C(O)—NH—(CH$_2$)$_{n2}$—CH$_3$. In a further embodiment, $R^2$ is OH, $R^3$ is H and $R^4$ is CH$_2$—NH—CH$_2$—PO$_3$H$_2$. In even a further embodiment, n1 is 1, 2 or 3, n2 is 9, 10, 11, 12, 13 or 14. In even a further embodiment, n1 is 2 and n2 is 10.

In one embodiment of a compound of Formula (II), or a pharmaceutically acceptable salt thereof, $R^1$ is —C(O)—(CH$_2$)$_{n2}$—CH$_3$. In a further embodiment, $R^2$ is OH, $R^3$ is H and $R^4$ is CH$_2$—NH—CH$_2$—PO$_3$H$_2$. In even a further embodiment, n2 is 9, 10, 11, 12, 13 or 14. In even a further embodiment, n2 is 10.

In one embodiment of a compound of Formula (II), or a pharmaceutically acceptable salt thereof, $R^1$ is —(CH$_2$)$_{n1}$—O—C(O)—(CH$_2$)$_{n2}$—CH$_3$ or —(CH$_2$)$_{n1}$—NH—C(O)—(CH$_2$)$_{n2}$—CH$_3$. In a further embodiment, $R^2$ is —NH—(CH$_2$)$_q$—$R^5$, $R^3$ is H and $R^4$ is H. In even a further embodiment, n1 is 1, 2 or 3, n2 is 9, 10, 11, 12, 13 or 14. In even a further embodiment, n1 is 2 and n2 is 10. In yet even a further embodiment, $R^1$ is —$(CH_2)_{n1}$—O—C(O)—$(CH_2)_{n2}$—$CH_3$. In yet even a further embodiment, q is 2 or 3 and $R^5$ is $N(CH_3)_2$.

In one embodiment of a compound of Formula (II), or a pharmaceutically acceptable salt thereof, $R^1$ is —$(CH_2)_{n1}$—NH—C(O)—$(CH_2)_{n2}$—$CH_3$. In a further embodiment, $R^2$ is —NH—$(CH_2)_q$—$R^5$, $R^3$ and $R^4$ are H. In even a further embodiment, n1 is 1, 2 or 3, n2 is 9, 10, 11, 12, 13 or 14. In even a further embodiment, n1 is 2 and n2 is 10. In yet even a further embodiment, q is 2 or 3 and $R^5$ is $N(CH_3)_2$.

In one embodiment of a compound of Formula (II), or a pharmaceutically acceptable salt thereof, $R^1$ is —$(CH_2)_{n1}$—O—C(O)—$(CH_2)_{n2}$—$CH_3$. In a further embodiment, $R^2$ is —NH—$(CH_2)_q$—$R^5$, $R^3$ and $R^4$ are H. In even a further embodiment, n1 is 1, 2 or 3, n2 is 9, 10, 11, 12, 13 or 14. In even a further embodiment, n1 is 2 and n2 is 10. In yet even a further embodiment, q is 2 or 3 and $R^5$ is $N(CH_3)_2$.

In one embodiment of a compound of Formula (II), or a pharmaceutically acceptable salt thereof, $R^1$ is —$(CH_2)_{n1}$—C(O)—O—$(CH_2)_{n2}$—$CH_3$. In a further embodiment, $R^2$ is —NH—$(CH_2)_q$—$R^5$, $R^3$ and $R^4$ are H. In even a further embodiment, n1 is 1, 2 or 3, n2 is 9, 10, 11, 12, 13 or 14. In even a further embodiment, n1 is 2 and n2 is 10. In yet even a further embodiment, q is 2 or 3 and $R^5$ is $N(CH_3)_2$.

In one embodiment of a compound of Formula (II), or a pharmaceutically acceptable salt thereof, $R^1$ is —$(CH_2)_{n1}$—C(O)—NH—$(CH_2)_{n2}$—$CH_3$. In a further embodiment, $R^2$ is —NH—$(CH_2)_q$—$R^5$, $R^3$ is H and $R^4$ is H. In even a further embodiment, n1 is 1, 2 or 3, n2 is 9, 10, 11, 12, 13 or 14. In even a further embodiment, n1 is 2 and n2 is 10. In yet even a further embodiment, q is 2 or 3 and $R^5$ is $N(CH_3)_2$.

In one embodiment of a compound of Formula (II), or a pharmaceutically acceptable salt thereof, $R^1$ is —C(O)—$(CH_2)_{n2}$—$CH_3$. In a further embodiment, $R^2$ is —NH—$(CH_2)_q$—$R^5$, $R^3$ is H and $R^4$ is H. In even a further embodiment, n2 is 9, 10, 11, 12, 13 or 14. In even a further embodiment, n2 is 10. In yet even a further embodiment, q is 2 or 3 and $R^5$ is $N(CH_3)_2$.

In yet another embodiment, a compound of Formula (I) or (II) is provided, wherein one or more hydrogen atoms is replaced with a deuterium atom. For example, in one embodiment of a compound of Formula (II), $R^3$ or $R^4$ is deuterium.

The compounds of present disclosure, i.e., the compounds of Formulae (I) and (II) can be prepared according to methods and steps known to those of ordinary skill in the art. For example, the compounds of the present may be prepared according to methods described in U.S. Pat. No. 6,392,012; U.S. Patent Application Publication No. 2017/0152291; U.S. Patent Application Publication No. 2016/0272682, each of which is hereby incorporated by reference in their entirety for all purposes. Methods described in International Publication No. WO 2018/08197, the disclosure of which is incorporated by reference in its entirety, can also be employed. Synthesis schemes are also provided at the Example section, herein.

Compositions provided herein can be in the form of a solution, suspension or dry powder. Compositions can be administered by techniques known in the art, including, but not limited to intramuscular, intravenous, intratracheal, intranasal, intraocular, intraperitoneal, subcutaneous, and transdermal routes. In addition, as discussed throughout, the compositions can also be administered via the pulmonary route, e.g., via inhalation with a nebulizer, a metered dose inhaler or a dry powder inhaler.

In one embodiment, the composition provided herein comprises a plurality of nanoparticles of the antibiotic of any of Formula (I)-(II) in association with a polymer. The mean diameter of the plurality of nanoparticles, in one embodiment, is from about 50 nm to about 900 nm, for example from about 10 nm to about 800 nm, from about 100 nm to about 700 nm, from about 100 nm to about 600 nm or from about 100 nm to about 500 nm.

In one embodiment, the plurality of nanoparticles comprise a biodegradable polymer and the glycopeptide antibiotic of Formulae (I)-(II). In a further embodiment, the biodegradable polymer is poly(D,L-lactide), poly(lactic acid) (PLA), poly(D,L-glycolide) (PLG), poly(lactide-co-glycolide) (PLGA), poly-(cyanoacrylate) (PCA), or a combination thereof.

In even a further embodiment, the biodegradable polymer is poly(lactic-co-glycolitic acid) (PLGA).

Nanoparticle compositions can be prepared according to methods known to those of ordinary skill in the art. For example, coacervation, solvent evaporation, emulsification, in situ polymerization, or a combination thereof can be employed (see, e.g., Soppimath et al. (2001). Journal of Controlled Release 70, pp. 1-20, incorporated by reference herein in its entirety).

The amount of polymer in the composition can be adjusted, for example, to adjust the release profile of the compound of Formula (I) or (II) from the composition.

In one embodiment, a dry powder composition disclosed in one of U.S. Pat. Nos. 5,874,064, 5,855,913 and/or U.S. Patent Application Publication No. 2008/0160092 is used to formulate one of the glycopeptides of Formula (I) or (II), or a pharmaceutically acceptable salt thereof. The disclosures of U.S. Pat. Nos. 5,874,064; 5,855,913 and U.S. Patent Application Publication No. 2008/0160092 are each incorporated by reference herein in their entireties.

In one embodiment, the composition delivered via the methods provided herein are spray dried, hollow and porous particulate compositions. For example, the hollow and porous particulate compositions as disclosed in WO 1999/16419, hereby incorporated in its entirety by reference for all purposes, can be employed. Such particulate compositions comprise particles having a relatively thin porous wall defining a large internal void, although, other void containing or perforated structures are contemplated as well.

Compositions delivered via the methods provided herein, in one embodiment, yield powders with bulk densities less than 0.5 g/cm$^3$ or 0.3 g/cm$^3$, for example, less 0.1 g/cm3, or less than 0.05 g/cm$^3$. By providing particles with very low bulk density, the minimum powder mass that can be filled into a unit dose container is reduced, which eliminates the need for carrier particles. Moreover, the elimination of carrier particles, without wishing to be bound by theory, can minimize throat deposition and any "gag" effect, since the large lactose particles can impact the throat and upper airways due to their size.

In some embodiments, the particulate compositions delivered via the methods provided herein comprise a structural matrix that exhibits, defines or comprises voids, pores, defects, hollows, spaces, interstitial spaces, apertures, perforations or holes. The particulate compositions in one embodiment, are provided in a "dry" state. That is, the particulate composition possesses a moisture content that allows the powder to remain chemically and physically stable during storage at ambient temperature and easily dispersible. As such, the moisture content of the microparticles is typically less than 6% by weight, and for example, less 3% by weight. In some embodiments, the moisture content is as low as 1% by weight. The moisture content is, at least in part, dictated by the formulation and is controlled by the process conditions employed, e.g., inlet temperature, feed concentration, pump rate, and blowing agent type, concentration and post drying.

Reduction in bound water can lead to improvements in the dispersibility and flowability of phospholipid based powders, leading to the potential for highly efficient delivery of powdered lung surfactants or particulate composition comprising active agent dispersed in the phospholipid.

The composition administered via the methods provided herein, in one embodiment, is a particulate composition comprising a compound of Formula (I) or (II), or a pharmaceutically acceptable salt thereof, a phospholipid and a polyvalent cation. In particular, the compositions of the present invention can employ polyvalent cations in phospholipid-containing, dispersible particulate compositions for pulmonary administration to the respiratory tract for local or systemic therapy via aerosolization.

Without wishing to be bound by theory, it is thought that the use of a polyvalent cation in the form of a hygroscopic salt such as calcium chloride stabilizes a dry powder prone to moisture induced stabilization. Without wishing to be bound by theory, it is thought that such cations intercalate the phospholipid membrane, thereby interacting directly with the negatively charged portion of the zwitterionic headgroup. The result of this interaction is increased dehydration of the headgroup area and condensation of the acyl-chain packing, all of which leads to increased thermodynamic stability of the phospholipids. Other benefits of such dry powder compositions are provided in U.S. Pat. No. 7,442,388, the disclosure of which is incorporated herein in its entirety for all purposes.

The polyvalent cation for use in the present invention in one embodiment, is a divalent cation. In a further embodiment, the divalent cation is calcium, magnesium, zinc or iron. The polyvalent cation is present in one embodiment, to increase the Tm of the phospholipid such that the particulate composition exhibits a Tm which is greater than its storage temperature Ts by at least 20° C. The molar ratio of polyvalent cation to phospholipid in one embodiment, is 0.05, e.g., from about 0.05 to about 2.0, or from about 0.25 to about 1.0. In one embodiment, the molar ratio of polyvalent cation to phospholipid is about 0.50. In one embodiment, the polyvalent cation is calcium and is provided as calcium chloride.

According to one embodiment, the phospholipid is a saturated phospholipid. In a further embodiment, the saturated phospholipid is a saturated phosphatidylcholine. Acyl chain lengths that can be employed range from about $C_{16}$ to $C_{22}$. For example, in one embodiment an acyl chain length of 16:0 or 18:0 (i.e., palmitoyl and stearoyl) is employed. In one phospholipid embodiment, a natural or synthetic lung surfactant is provided as the phospholipid component. In this embodiment, the phospholipid can make up to 90 to 99.9% w/w of the lung surfactant. Suitable phospholipids according to this aspect of the invention include natural or synthetic lung surfactants such as those commercially available under the trademarks ExoSurf, InfaSurf® (Ony, Inc.), Survanta, CuroSurf, and ALEC.

The Tm of the phospholipid-glycopeptide particles, in one embodiment, is manipulated by varying the amount of polyvalent cations in the composition.

Phospholipids from both natural and synthetic sources are compatible with the compositions administered by the methods provided herein, and may be used in varying concentrations to form the structural matrix. Generally compatible phospholipids comprise those that have a gel to liquid crystal phase transition greater than about 40° C. The incorporated phospholipids in one embodiment, are relatively long chain (i.e., $C_{16}$-$C_{22}$) saturated lipids and in a further embodiment, comprise saturated phospholipids. In even a further embodiment, the saturated phospholipid is a saturated phosphatidylcholine. In even a further embodiment, the saturated phosphatidylcholine has an acyl chain lengths of 16:0 or 18:0 (palmitoyl or stearoyl). Exemplary phospholipids useful in the disclosed stabilized preparations comprise, phosphoglycerides such as dipalmitoylphosphatidylcholine (DPPC), disteroylphosphatidylcholine (DSPC), diarachidoylphosphatidylcholine dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, long-chain saturated phosphatidylinositols.

In addition to the phospholipid, a co-surfactant or combinations of surfactants, including the use of one or more in the liquid phase and one or more associated with the particulate compositions can be used in the compositions delivered via the methods provided herein. By "associated with or comprise" it is meant that the particulate compositions may incorporate, adsorb, absorb, be coated with or be formed by the surfactant. Surfactants include fluorinated and nonfluorinated compounds and can include saturated and unsaturated lipids, nonionic detergents, nonionic block copolymers, ionic surfactants and combinations thereof. In one embodiment comprising stabilized dispersions, nonfluorinated surfactants are relatively insoluble in the suspension medium.

Compatible nonionic detergents suitable as co-surfactants in the compositions provided herein include sorbitan esters including sorbitan trioleate (Span™ 85), sorbitan sesquioleate, sorbitan monooleate, sorbitan monolaurate, polyoxyethylene (20) (Brij® S20), sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Block copolymers include diblock and triblock copolymers of polyoxyethylene and polyoxypropylene, including poloxamer 188 (Pluronic® F-68), poloxamer 407 (Pluronic® F-127), and poloxamer 338. Ionic surfactants such as sodium sulfosuccinate, and fatty acid soaps may also be utilized.

The phospholipid-glycopeptide particulate compositions can include additional lipids such as a glycolipid, ganglioside GM1, sphingomyelin, phosphatidic acid, cardiolipin; a lipid bearing a polymer chain such as polyethylene glycol, chitin, hyaluronic acid, or polyvinylpyrrolidone; a lipid bearing sulfonated mono-, di-, and polysaccharides; a fatty acid such as palmitic acid, stearic acid, and/or oleic acid; cholesterol, cholesterol esters, and cholesterol hemisuccinate.

In addition to the phospholipid and polyvalent cation, the particulate composition delivered via the methods provided herein can also include a biocompatible, and in some embodiments, biodegradable polymer, copolymer, or blend or other combination thereof. The polymer in one embodiment is a polylactide, polylactide-glycolide, cyclodextrin, polyacrylate, methylcellulose, carboxymethylcellulose, polyvinyl alcohol, polyanhydride, polylactam, polyvinyl pyrrolidone, polysaccharide (e.g., dextran, starch, chitin, chitosan), hyaluronic acid, protein (e.g., albumin, collagen, gelatin, etc.).

Besides the aforementioned polymer materials and surfactants, other excipients can be added to a particulate composition, for example, to improve particle rigidity, production yield, emitted dose and deposition, shelf-life and/or patient acceptance. Such optional excipients include, but are not limited to: coloring agents, taste masking agents, buffers, hygroscopic agents, antioxidants, and chemical stabilizers. Other excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Mixtures of carbohydrates and amino acids are further held to be within the scope of the present invention. The inclusion of both inorganic (e.g., sodium chloride), organic acids and their salts (e.g., carboxylic acids and their salts such as sodium citrate, sodium ascorbate, magnesium gluconate, sodium gluconate, tromethamine hydrochloride, etc.) and buffers can also be undertaken. Salts and/or organic solids such as ammonium carbonate, ammonium acetate, ammonium chloride or camphor can also be employed.

According to one embodiment, the particulate compositions may be used in the form of dry powders or in the form of stabilized dispersions comprising a non-aqueous phase. The dispersions or powders of the present invention may be used in conjunction with metered dose inhalers (MDIs), dry powder inhalers (DPIs), atomizers, or nebulizers to provide for pulmonary delivery.

While several procedures are generally compatible with making certain dry powder compositions described herein, spray drying is a particularly useful method. As is well known, spray drying is a one-step process that converts a liquid feed to a dried particulate form. With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference in its entirety for all purposes. In general, spray drying consists of bringing together a highly dispersed liquid, and a sufficient volume of hot air to produce evaporation and drying of the liquid droplets. The preparation to be spray dried or feed (or feed stock) can be any solution, suspension, slurry, colloidal dispersion, or paste that may be atomized using the selected spray drying apparatus. In one embodiment, the feed stock comprises a colloidal system such as an emulsion, reverse emulsion, microemulsion, multiple emulsion, particulate dispersion, or slurry. Typically, the feed is sprayed into a current of warm filtered air that evaporates the solvent and conveys the dried product to a collector. The spent air is then exhausted with the solvent.

It will further be appreciated that spray dryers, and specifically their atomizers, may be modified or customized for specialized applications, e.g., the simultaneous spraying of two solutions using a double nozzle technique. More specifically, a water-in-oil emulsion can be atomized from one nozzle and a solution containing an anti-adherent such as mannitol can be co-atomized from a second nozzle. In one embodiment, it may be desirable to push the feed solution though a custom designed nozzle using a high pressure liquid chromatography (HPLC) pump. Examples of spray drying methods and systems suitable for making the dry powders of the present invention are disclosed in U.S. Pat. Nos. 6,077,543, 6,051,256, 6,001,336, 5,985,248, and 5,976,574, each of which is incorporated in their entirety by reference.

While the resulting spray-dried powdered particles typically are approximately spherical in shape, nearly uniform in size and frequently are hollow, there may be some degree of irregularity in shape depending upon the incorporated glycopeptide of Formulae (I)-(II) and the spray drying conditions. In one embodiment, an inflating agent (or blowing agent) is used in the spray-dried powder production, e.g., as disclosed in WO 99/16419, incorporated by reference herein in its entirety for all purposes. Additionally, an emulsion can be included with the inflating agent as the disperse or continuous phase. The inflating agent can be dispersed with a surfactant solution, using, for instance, a commercially available microfluidizer at a pressure of about 5000 to 15,000 PSI. This process forms an emulsion, and in some embodiments, an emulsion stabilized by an incorporated surfactant, and can comprise submicron droplets of water immiscible blowing agent dispersed in an aqueous continuous phase. The blowing agent in one embodiment, is a fluorinated compound (e.g., perfluorohexane, perfluorooctyl bromide, perfluorooctyl ethane, perfluorodecalin, perfluorobutyl ethane) which vaporizes during the spray-drying process, leaving behind generally hollow, porous aerodynamically light microspheres. Other suitable liquid blowing agents include nonfluorinated oils, chloroform, Freons, ethyl acetate, alcohols and hydrocarbons. Nitrogen and carbon dioxide gases are also contemplated as a suitable blowing agent. Perfluorooctyl ethane is the blowing agent, in one embodiment.

Whatever components are selected, the first step in particulate production in one embodiment, comprises feed stock preparation. The selected glycopeptide is dissolved in a solvent, for example water, dimethylformamide (DMF), dimethyl sulfoxide (DMSO), acetonitrile, ethanol, methanol, or combinations thereof, to produce a concentrated solution. The polyvalent cation may be added to the glycopeptide solution or may be added to the phospholipid emulsion as discussed below. The glycopeptide may also be dispersed directly in the emulsion, particularly in the case of water insoluble agents. Alternatively, the glycopeptide is incorporated in the form of a solid particulate dispersion. The concentration of the glycopeptide used is dependent on the amount of glycopeptide required in the final powder and the performance of the delivery device employed (e.g., the fine particle dose for a MDI or DPI). As needed, cosurfactants such as poloxamer 188 or span 80 may be dispersed into this annex solution. Additionally, excipients such as sugars and starches can also be added.

In one embodiment, a polyvalent cation-containing oil-in-water emulsion is then formed in a separate vessel. The oil employed in one embodiment, is a fluorocarbon (e.g., perfluorooctyl bromide, perfluorooctyl ethane, perfluorodecalin) which is emulsified with a phospholipid. For example, polyvalent cation and phospholipid may be homogenized in hot distilled water (e.g., 60° C.) using a suitable high shear mechanical mixer (e.g., Ultra-Turrax model T-25 mixer) at 8000 rpm for 2 to 5 minutes. In one embodiment, 5 to 25 g of fluorocarbon is added dropwise to the dispersed surfactant solution while mixing. The resulting polyvalent cation-containing perfluorocarbon in water emulsion is then processed using a high pressure homogenizer to reduce the particle size. In one embodiment, the emulsion is processed at 12,000 to 18,000 PSI, 5 discrete passes and kept at 50 to 80° C.

The glycopeptide solution (or suspension) and perfluorocarbon emulsion are then combined and fed into the spray dryer. In one embodiment, the two preparations are miscible. While the glycopeptide is solubilized separately for the purposes of the instant discussion it will be appreciated that, in other embodiments, the glycopeptide may be solubilized (or dispersed) directly in the emulsion. In such cases, the glycopeptide emulsion is simply spray dried without combining a separate glycopeptide preparation.

Operating conditions such as inlet and outlet temperature, feed rate, atomization pressure, flow rate of the drying air, and nozzle configuration can be adjusted in accordance with the manufacturer's guidelines in order to produce the desired particle size, and production yield of the resulting dry particles. The selection of appropriate apparatus and processing conditions are well within the purview of a skilled artisan. In one embodiment, the particulate composition comprises hollow, porous spray dried micro- or nano-particles.

Along with spray drying, particulate compositions useful in the present invention may be formed by lyophilization. Those skilled in the art will appreciate that lyophilization is a freeze-drying process in which water is sublimed from the composition after it is frozen. Methods for providing lyophilized particulates are known to those of skill in the art. The lyophilized cake containing a fine foam-like structure can be micronized using techniques known in the art.

Besides the aforementioned techniques, the glycopeptide particulate compositions or glycopeptide particles provided herein may also be formed using a method where a feed solution (either emulsion or aqueous) containing wall forming agents is rapidly added to a reservoir of heated oil (e.g., perflubron or other high boiling FCs) under reduced pressure. The water and volatile solvents of the feed solution rapidly boils and are evaporated. This process provides a perforated structure from the wall forming agents similar to puffed rice or popcorn. In one embodiment, the wall forming agents are insoluble in the heated oil. The resulting particles can then be separated from the heated oil using a filtering technique and subsequently dried under vacuum.

In another embodiment, the particulate compositions of the present invention may also be formed using a double emulsion method. In the double emulsion method, the medicament is first dispersed in a polymer dissolved in an organic solvent (e.g., methylene chloride, ethyl acetate) by sonication or homogenization. This primary emulsion is then stabilized by forming a multiple emulsion in a continuous aqueous phase containing an emulsifier such as polyvinylalcohol. Evaporation or extraction using conventional techniques and apparatus then removes the organic solvent. The resulting particles are washed, filtered and dried prior to combining them with an appropriate suspension medium.

In order to maximize dispersibility, dispersion stability and optimize distribution upon administration, the mean geometric particle size of the particulate compositions in one embodiment, is from about 0.5-50 µm, for example from about 0.5 µm to about 10 µm or from about 0.5 to about 5 µm. In one embodiment, the mean geometric particle size (or diameter) of the particulate compositions is less than 20 µm or less than 10 µm. In a further embodiment, the mean geometric diameter is ≤about 7 µm or ≤5 µm. In even a further embodiment, the mass geometric diameter is ≤about 2.5 µm. In one embodiment, the particulate composition comprises a powder of dry, hollow, porous spherical shells of from about 0.1 to about 10 µm, e.g., from about 0.5 to about 5 µm in diameter, with shell thicknesses of approximately 0.1 µm to approximately 0.5 µm.

Methods for treating infectious diseases, especially those caused by Gram-positive microorganisms, are provided. The method comprises, in one embodiment, administering to a patient in need of treatment, a composition comprising an effective amount of an LGPC derivative, or a pharmaceutically acceptable salt thereof. The LGPC derivative, contains a primary amino conjugated lipophilic moiety that is cleavable by enzymatic hydrolysis. The lipophilic moiety is conjugated to the primary amino group via a functional group that is capable of undergoing enzymatic hydrolysis. The functional group that undergoes enzymatic hydrolysis, in one embodiment, in conjugated to the primary amino group via a straight chain or branched alkyl group, e.g., a methyl, ethyl, propyl or butyl group. In another embodiment, the functional group is an amide that comprises the nitrogen atom from the primary amino group of the glycopeptide. The method comprises, in one embodiment, administering the composition comprising the LGPC derivative to the patient in need of treatment via inhalation.

In one embodiment of the methods provided herein, a composition comprising an effective amount of a compound of Formula (I) or (II), or a pharmaceutically acceptable salt of one of the foregoing, is administered to a patient in need of treatment.

Without wishing to be bound by a particular theory, it is believed that the $R^1$ groups conjugated to the glycopeptides provided herein facilitate cellular uptake of the glycopeptide at the site of infection, for example, macrophage uptake.

An "effective amount" of a compound of Formula (I) or (II) or a pharmaceutically acceptable salt of Formula (I) or (II), is an amount that can provide the desired therapeutic response. The effective amount can refer to a single dose as part of multiple doses during an administration period, or as the total dosage of the LGPC given during an administration period. A treatment regimen can include substantially the same dose for each LGPC administration, or can comprise at least one, at least two or at least three different dosages.

According to one embodiment, a method is provided to treat an infection due to a Gram-positive bacterium, including, but not limited to, genera *Staphylococcus, Streptococcus, Enterococcus, Bacillus, Corynebacleriutn, Nocardia, Clostridium*, and *Listeria*. In one embodiment, the infection is due to a Gram-positive cocci bacterium. In a further embodiment, the Gram-positive cocci infection is a *Staphylococcus, Enterococcus* or *Streptococcus* infection.

The bacterial infection treated by the methods provided herein may be present as planktonic free-floating bacteria, a biofilm, or a combination thereof. In one embodiment, the infection treated with the methods provided herein is a pulmonary infection.

In one embodiment, the bacterial infection is a Gram-positive bacterial infection. In a further embodiment, the bacterial infection is a pulmonary Gram-positive bacterial infection.

In one embodiment, the Gram-positive bacterial infection is a Gram-positive cocci infection. In a further embodiment, the Gram-positive cocci infection is a *Streptococcus, Enterococcus* or a *Staphylococcus* infection.

Over the past few decades, there has been a decrease in the susceptibility of Gram-positive cocci to antibacterials for the treatment of infection. See, e.g., Alvarez-Lerma et al. (2006) Drugs 66, pp. 751-768, incorporated by reference herein in its entirety for all purposes. As such, in one aspect, the present invention addresses this need by providing a composition comprising an effective amount of a compound of Formula (I) or (II), or a pharmaceutically acceptable salt thereof, in a method for treating a patient in need thereof for a Gram-positive cocci infection that is resistant to a different antibacterial. For example, in one embodiment, the Gram-positive cocci infection is a penicillin resistant or a vancomycin resistant bacterial infection. In a further embodiment, the resistant bacterial infection is a methicillin-resistant *Staphylococcus* infection, e.g., methicillin-resistant *S. aureus* or a methicillin-resistant *Staphylococcus epidermidis* infection. In another embodiment, the resistant bacterial infection is an oxacillin-resistant *Staphylococcus* (e.g., *S. aureus*) infection, a vancomycin-resistant *Enterococcus* infection or a penicillin-resistant *Streptococcus* (e.g., *S. pneumoniae*) infection. In yet another embodiment, the Gram-positive cocci infection is a vancomycin-resistant enterococci (VRE), methicillin-resistant *Staphylococcus aureus* (MRSA), methicillin-resistant *Staphylococcus epidermidis* (MRSE), vancomycin resistant *Enterococcus faecium* also resistant to teicoplanin (VRE Fm Van A), vancomycin resistant *Enterococcus faecium* sensitive to teicoplanin (VRE Fm Van B), vancomycin resistant *Enterococcus faecalis* also resistant to teicoplanin (VRE Fs Van A), vancomycin resistant *Enterococcus faecalis* sensitive to teicoplanin (VRE Fs Van B), or penicillin-resistant *Streptococcus pneumoniae* (PSRP).

According to one embodiment, a method is provided for treating a bacterial infection comprising administering a composition comprising an effective amount of a compound of Formula (I) or (II), or a pharmaceutically-acceptable salt thereof, to the patient. For example, the composition can be administered to the patient via pulmonary administration or via parenteral administration (e.g., intravenous).

As provided herein, LGPC derivatives of Formulae (I) and (II) are provided. Such compounds are useful in the treatment of bacterial infections, including, but not limited to, pulmonary infections, and specifically, pulmonary infections caused by Gram-positive bacteria. The LGPC derivatives provided herein possess a biologically-labile moiety (e.g., amide, ester) connected via an amine group of the glycopeptide, e.g., a primary amine. Subsequent to administration, the biologically-labile moiety undergoes cleavage by any available mechanism (e.g., hydrolysis or enzymatic cleavage), providing one or more glycopeptide metabolites. In some embodiments, the glycopeptide metabolite provides a decreased residence time in the lungs compared to the unmetabolized glycopeptide compound, thereby assisting in elimination of the therapeutic agent from this organ.

In one embodiment, the compound of Formula (I) or (II), and its respective metabolite, provide a synergistic effect against the bacterial infection being treated.

Metabolites of LGPC derivatives of Formula (I) (or a pharmaceutically acceptable salt thereof), in one embodiment, have the following structures (Glycopeptide, $R^1$, n1 and n2 as defined above).

Glycopeptide-$(CH_2)_{n1}$—OH (a metabolite of a compound of Formula (I), where $R^1$ is —$(CH_2)_{n1}$—O—C(O)—$(CH_2)_{n2}$—$CH_3$; —$(CH_2)_{n1}$—O—C(O)—O—$(CH_2)_{n2}$—$CH_3$; or —$(CH_2)_{n1}$—O—C(O)—NH—$(CH_2)_{n2}$—$CH_3$)

Glycopeptide-$(CH_2)_{n1}$—$NH_2$ (metabolite of a compound of Formula (I), where $R^1$ is —$(CH_2)_{n1}$—NH—C(O)—$(CH_2)_{n2}$—$CH_3$; or —$(CH_2)_{n1}$—NH—C(O)—O—$(CH_2)_{n2}$—$CH_3$)

Glycopeptide-$(CH_2)_{n1}$—C(O)OH (a metabolite of a compound of Formula (I), where $R^1$ is —$(CH_2)_{n1}$—C(O)—NH—$(CH_2)_{n2}$—$CH_3$ or —$(CH_2)_{n1}$—C(O)—O—$(CH_2)_{n2}$—$CH_3$)

Metabolites of LGPC derivatives of Formula (II) (or a pharmaceutically acceptable salt thereof), have the following structures ($R^1$, $R^2$, $R^3$, $R^4$, n1 and n2 defined above):

Metabolite 1

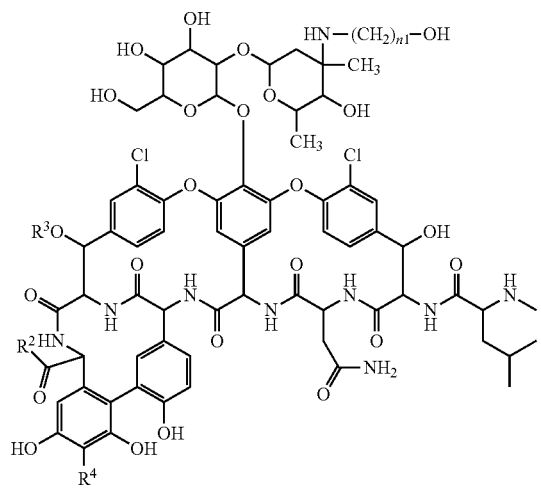

a metabolite of a compound of Formula (II), where $R^1$ is

—$(CH_2)_{n1}$—O—C(O)—$(CH_2)_{n2}$-$CH_3$;
—$(CH_2)_{n1}$—O—C(O)—O—$(CH_2)_{n2}$-$CH_3$; or
—$(CH_2)_{n1}$—O—C(O)—NH—$(CH_2)_{n2}$-$CH_3$)

Metabolite 2

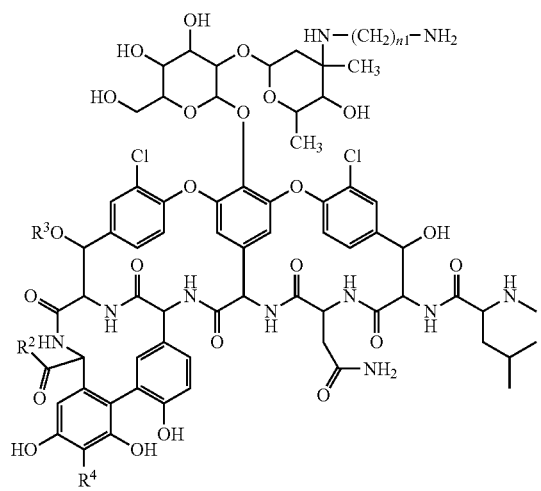

a metabolite of a compound of Formula (II), where $R^1$ is

—$(CH_2)_{n1}$-NH-C(O)—$(CH_2)_{n2}$-$CH_3$ or
—$(CH_2)_{n1}$-NH-C(O)—O—$(CH_2)_{n2}$-$CH_3$)

-continued

Metabolite 3

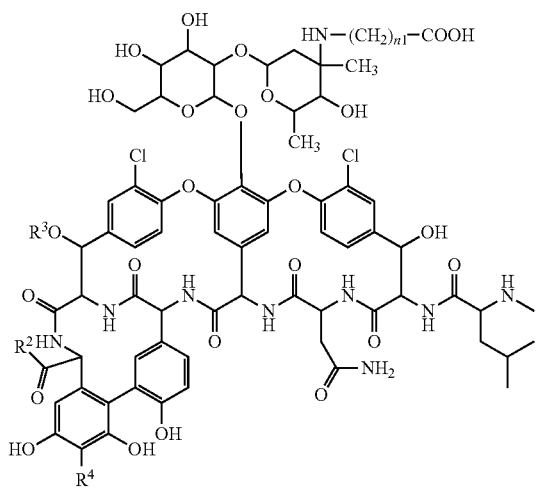

a metabolite of a compound of Formula (II), where $R^1$ is

—$(CH_2)_{n1}$—C(O)NH—$(CH_2)_{n2}$—$CH_3$ or
—$(CH_2)_{n1}$—C(O)O—$(CH_2)_{n2}$—$CH_3$

In one embodiment, a Gram-positive cocci infection is treated with one of the methods provided herein. In a further embodiment, the Gram-positive cocci infection is a *Staphylococcus* infection. *Staphylococcus* is Gram-positive non-motile bacteria that colonizes skin and mucus membranes. Staphylococci are spherical and occur in microscopic clusters resembling grapes. The natural habitat of *Staphylococcus* is nose; it can be isolated in 50% of normal individuals. 20% of people are skin carriers and 10% of people harbor *Staphylococcus* in their intestines. Examples of Staphylococci infections treatable with the methods and compositions provided herein, include *S. aureus, S. epidermidis, S. auricularis, S. carnosus, S. haemolyticus, S. hyicus, S. intermedius, S. lugdunensis, S. saprophytics, S. sciuri, S. simulans*, and *S. wameri*. In one embodiment, the *Staphylococcus* infection is a *Staphylococcus aureus* (*S. aureus*) infection.

While there have been about 20 species of *Staphylococcus* reported, only *Staphylococcus aureus* and *Staphylococcus epidermis* are known to be significant in their interactions with humans.

In one embodiment, the *Staphylococcus* infection is a *Staphylococcus haemolyticus* (*S. haemolyticus*) infection. In another embodiment, the *Staphylococcus* infection is a *Staphylococcus epidermis* (*S. epidermis*) infection. A *Staphylococcus* infection, e.g., *S. aureus* is treated in one embodiment, in a patient that has been diagnosed with mechanical ventilation-associated pneumonia.

In one embodiment, the *S. aureus* infection is a methicillin-resistant *Staphylococcus aureus* (MRSA) infection. In another embodiment, the *S. aureus* infection is a methicillin-sensitive *S. aureus* (MSSA) infection. In another embodiment, the *S. aureus* infection is a *S. aureus* (VISA) infection, or a vancomycin-resistant *S. aureus* (VRSA) infection.

In one embodiment, the *Staphylococcus* species is resistant to a penicillin such as methicillin. In a further embodiment, the *Staphylococcus* species is methicillin-resistant *Staphylococcus aureus* (MRSA) or methicillin-resistant *Staphylococcus epidermidis* (MRSE). The *Staphylococcus* species, in another embodiment, is methicillin-sensitive *S. aureus* (MSSA), vancomycin-intermediate *S. aureus* (VISA), or vancomycin-resistant *S. aureus* (VRSA).

*S. aureus* colonizes mainly the nasal passages, but it may be found regularly in most anatomical locales, including skin oral cavity, and gastrointestinal tract. In one embodiment, a *S. aureus* infection is treated with one of the methods and/or compositions provided herein.

The *S. aureus* infection can be a healthcare associated, i.e., acquired in a hospital or other healthcare setting, or community-acquired.

In one embodiment, the Staphylococcal infection treated with one of the methods and/or compositions provided herein, causes endocarditis or septicemia (sepsis). As such, the patient in need of treatment with one of the methods and/or compositions provided herein, in one embodiment, is an endocarditis patient. In another embodiment, the patient is a septicemia (sepsis) patient.

In one embodiment, the bacterial infection is erythromycin-resistant (erm$^R$), vancomycin-intermediate *S. aureus* (VISA) heterogeneous vancomycin-intermediate *S. aureus* (hVISA), *S. epidermidis* coagulase-negative staphylococci (CoNS), penicillin-intermediate *S. pneumoniae* (PISP), or penicillin-resistant *S. pneumoniae* (PRSP). In even a further embodiment, the administering comprises administering via inhalation.

In one embodiment, the Gram-positive cocci infection is a *Streptococcus* infection. Streptococci are Gram-positive, non-motile cocci that divide in one plane, producing chains of cells. The primary pathogens include *S. pyrogenes* and *S. pneumoniae* but other species can be opportunistic. *S. pyrogenes* is the leading cause of bacterial pharyngitis and tonsillitis. It can also produce sinusitis, otitis, arthritis, and bone infections. Some strains prefer skin, producing either superficial (impetigo) or deep (cellulitis) infections. *Streptococcus pnemoniae* is treated, in one embodiment, in a patient that has been diagnosed with community-acquired pneumonia or purulent meningitis.

*S. pneumoniae* is the major cause of bacterial pneumonia in adults, and in one embodiment, an infection due to *S. pneumoniae* is treated via one of the methods and/or compositions provided herein. Its virulence is dictated by its capsule. Toxins produced by streptococci include: streptolysins (S & O), NADase, hyaluronidase, streptokinase, DNAses, erythrogenic toxin (which causes scarlet fever rash by producing damage to blood vessels; requires that bacterial cells are lysogenized by phage that encodes toxin). Examples of *Streptococcus* infections treatable with the compositions and methods provided herein include, *S. agalactiae, S. anginosus, S. bovis, S. canis, S. constellatus, S. dysgalactiae, S. equi, S. equinus, S. mae, S. intermedins, S. mitis, S. mutans, S. oralis, S. parasanguinis, S. peroris, S. pneumoniae, S. pyogenes, S. ratti, S. salivarius, S. salivarius ssp. thermophilies, S. sanguinis, S. sobrinus, S. suis, S. uteris, S. vestibularis, S. viridans*, and *S. zooepidemicus*.

In one embodiment, the *Streptococcus* infection is a *S. pyogenes, S. agalactiae, S. dysgalactiae, S. bovis, S. anginosus, S. sanguinis, S. suis, S. mitis, S. pneumoniae*, or a *S. mutans* infection. In another embodiment, the *Streptococcus* infection is a *S. mutans* infection. In still another embodiment, the *Streptococcus* infection is a *S. pneumoniae* infection. In yet another embodiment, the *Streptococcus* infection is a *S. dysgalactiae* infection. In a further embodiment, the *Streptococcus* infection is a *S. pyogenes* infection.

In one embodiment, the Gram-positive cocci infection is an *Enterococcus* infection. In another embodiment, the *Enterococcus* infection is a vancomycin resistant infection (VRE). In a further embodiment, the *Enterococcus* infection is a vancomycin sensitive infection (VSE).

The genus Enterococci consists of Gram-positive, facultatively anaerobic organisms that are ovoid in shape and appear on smear in short chains, in pairs, or as single cells. Enterococci are important human pathogens that are increasingly resistant to antimicrobial agents. Examples of Enterococci treatable with the methods and compositions provided herein are *E. avium, E. durans, E. faecalis, E. faecium, E. gallinarum*, and *E. solitarius*. An *Enterococcus* species is treated, in one embodiment, in a patient that has been diagnosed with a urinary-catheter related infection.

In one embodiment of the methods provided herein, a patient in need thereof is treated for an *Enterococcus faecalis* (*E. faecalis*) infection. In a further embodiment, the infection is a pulmonary infection. In another embodiment, a patient in need thereof is treated for an *Enterococcus faecium* (*E. faecium*) infection. In a further embodiment, the infection is a pulmonary infection.

In one embodiment, a patient in need thereof is treated for an *Enterococcus* infection that is resistant or sensitive to vancomycin or resistant or sensitive to penicillin. In a further embodiment, the *Enterococcus* infection is an *E. faecalis* or *E. faecium* infection. In a specific embodiment, the *Enterococcus* infection is an *Enterococcus faecalis* (*E. faecalis*) infection. In one embodiment, the *E. faecalis* infection is a vancomycin-sensitive *E. faecalis* infection. In another embodiment, the *E. faecalis* infection is a vancomycin-resistant *E. faecalis* infection. In yet another embodiment, the *E. faecalis* infection is an ampicillin-resistant *E. faecalis* infection. In another embodiment, the *Enterococcus* infection is an *Enterococcus faecium* (*E. faecium*) infection In still another embodiment, the *E. faecium* infection is a vancomycin-resistant *E. faecium* infection. In a further embodiment, the *E. faecium* infection is an ampicillin-resistant *E. faecium* infection. In yet a further embodiment, the *E. faecium* infection is a vancomycin-sensitive *E. faecium* infection.

Bacteria of the genus *Bacillus* are aerobic, endospore-forming, Gram-positive rods, and infections due to such bacteria are treatable via the methods and compositions provided herein. *Bacillus* species can be found in soil, air, and water where they are involved in a range of chemical transformations. In one embodiment, a method is provided herein to treat a *Bacillus anthracis* (*B. anthracis*) infection with a glycopeptide composition. *Bacillus anthracis*, the infection that causes Anthrax, is acquired via direct contact with infected herbivores or indirectly via their products. The clinical forms include cutaneous anthrax, from handling infected material, intestinal anthrax, from eating infected meat, and pulmonary anthrax from inhaling spore-laden dust. The route of administration of the glycopeptide will vary depending on how the patient acquires the *B. anthracis* infection. For example, in the case of pulmonary anthrax, the patient, in one embodiment, is treated via a dry powder inhaler, nebulizer or metered dose inhaler.

Several other *Bacillus* species, in particular, *B. cereus, B. subtilis* and *B. licheniformis*, are associated periodically with bacteremia/septicemia, endocarditis, meningitis, and infections of wounds, the ears, eyes, respiratory tract, urinary tract, and gastrointestinal tract, and are therefore treatable with the methods and compositions provided herein. Examples of pathogenic *Bacillus* species whose infection is treatable with the methods and compositions provided herein, include, but are not limited to, *B. anthracis, B. cereus* and *B. coagulans*.

Corynebacteria are small, generally non-motile, Gram-positive, non sporalating, pleomorphic bacilli and infections due to these bacteria are treatable via the methods provided herein. *Corybacterium diphtheria* is the etiological agent of diphtheria, an upper respiratory disease mainly affecting children, and is treatable via the methods and compositions provided herein. Examples of other Corynebacteria species treatable with the methods and compositions provided herein include *Corynebacterium diphtheria, Corynebacterium pseudotuberculosis, Corynebacterium tenuis, Corynebacterium striatum*, and *Corynebacterium minutissimum*.

The bacteria of the genus *Nocardia* are Gram-positive, partially acid-fast rods, which grow slowly in branching chains resembling fungal hyphae. Three species cause nearly all human infections: *N. asteroides, N. brasiliensis*, and *N. caviae*, and patients with such infections can be treated with the compositions and methods provided herein. Infection is by inhalation of airborne bacilli from an environmental source (soil or organic material). Other Nocardial species treatable with the methods and compositions provided herein include *N. aerocolonigenes, N. africana, N. argentinensis, N. asteroides, N. blackwellu, N. brasiliensis, N. brevicalena, N. cornea, N. caviae, N. cerradoensis, N. corallina, N. cyriacigeorgica, N. dassonvillei, N. elegans, N. farcinica, N. nigiitansis, N. nova, N. opaca, N. otitidiscavarium, N. paucivorans, N. pseudobrasiliensis, N. rubra, N. transvelencesis, N. uniformis, N. vaccinii*, and *N. veterana*.

Clostridia are spore-forming, Gram-positive anaerobes, and infections due to such bacteria are treatable via the methods and compositions provided herein. In one embodiment, one of the methods provided herein are used to treat a *Clostridium tetani* (*C. tetani*) infection, the etiological agent of tetanus. In another embodiment, one of the methods provided herein is used to treat a *Clostridium botidinum* (*C. botidinum*) infection, the etiological agent of botulism. In yet another embodiment, one of the methods provided herein is used to treat a *C. perfringens* infection, one of the etiological agents of gas gangrene. Other *Clostridium* species treatable with the methods and compositions of the present invention, include, *C. difficile, C. perfringens*, and/or *C. sordellii*. In one embodiment, the infection to be treated is a *C. difficile* infection.

*Listeria* are non-spore-forming, nonbranching Gram-positive rods that occur individually or form short chains. *Listeria monocytogenes* (*L. monocytogenes*) is the causative agent of listeriosis, and in one embodiment, a patient infected with *L. monocytogenes* is treated with one of the methods and compositions provided herein. Examples of *Listeria* species treatable with the methods and compositions provided herein, include *L. grayi, L. innocua, L. ivanovii, L. monocytogenes, L. seeligeri, L. murrayi*, and *L. welshimeri*.

In some embodiments, the methods disclosed herein are useful in treating Gram-negative infections. In one embodiment, the bacterial infection is a *Burkholderia* infection. In some embodiments, the *Burkholderia* infection is a *Burkholderia pseudomallei* (*B. pseudomallei*), *B. dolosa, B. fungorum, B. gladioli, B. multivorans, B. vietnamiensis, B. ambifaria, B. andropogonis, B. anthina, B. brasilensis, B. calcdonica, B. caribensis* or a *B. caryophylli* infection.

*Burkholderia* is a genus of Proteobacteria whose pathogenic members include among other the *Burkholderia cepacia* complex which attacks humans; *Burkholderia pseudomallei*, causative agent of melioidosis; and *Burkholderia cepacia*, an important pathogen of pulmonary infections in people with cystic fibrosis. The *Burkholderia* (previously part of *Pseudomonas*) genus name refers to a group of virtually ubiquitous Gram-negative, obligately aerobic, rod-shaped bacteria that are motile by means of single or multiple polar flagella, with the exception of *Burkholderia mallei* which is nonmotile.

In other embodiment, the bacterial infection is a *Yersinia pestis* (*Y. pestis*) infection.

*Yersinia pestis* (formerly *Pasteurella pestis*) is a Gram-negative, rod-shaped coccobacillus, non-mobile with no spores. It is a facultative anaerobic organism that can infect humans via the oriental rat flea. It causes the disease plague, which takes three main forms: pneumonic, septicemic, and bubonic plagues.

In yet another embodiment, the bacterial infection is a *Francisella tularensis* (*F. tularensis*) infection. *Francisella tularensis* is a pathogenic species of Gram-negative, rod-shaped coccobacillus, an aerobe bacterium. It is non-spore forming, non-motile and the causative agent of tularemia, the pneumonic form of which is often lethal without treatment. It is a fastidious, facultative intracellular bacterium which requires cysteine for growth.

The bacterial infection in one embodiment, is a respiratory tract infection. In a further embodiment, the infection is a resistant bacterial infection, for example, one of the infections provided above. The patient treatable by the methods and compositions provided herein, in one embodiment, has been diagnosed with a community-acquired respiratory tract infection, for example, pneumonia. In one embodiment, the bacterial infection treated in the pneumonia patient is a *S. pneumoniae* infection. In another embodiment, the bacterial infection treated in the pneumonia patient is *Mycoplasma* pneumonia or a *Legionella* species. In another embodiment, the bacterial infection in the pneumonia patient is penicillin resistant, e.g., penicillin-resistant *S. pneumoniae*.

The bacterial infection, in one embodiment, is a hospital acquired infection (HAI), or acquired in another health care facility, e.g., a nursing home, rehabilitation facility, outpatient clinic, etc. Such infections are also referred to as nosocomial infections. In a further embodiment, the bacterial infection is a respiratory tract infection or a skin infection. In one embodiment, the HAI is pneumonia. In a further embodiment, the pneumonia is due to *S. aureus*, e.g., MRSA.

Respiratory infections and in particular pulmonary infections are quite problematic for patients afflicted with cystic fibrosis (CF). In fact, such infections are the main cause of pulmonary deterioration in this population of patients. The lungs of CF patients are colonized and infected by bacteria from an early age. These bacteria thrive in the altered mucus, which collects in the small airways of the lungs. The formation of biofilms makes infections of this origin difficult to treat. Consequently, more robust treatments options are needed. Thus, in one embodiment, the methods disclosed herein are useful in treating a patient with cystic fibrosis having a bacterial infection. In some embodiments, the bacterial infection is a pulmonary infection. In other embodiments, the pulmonary infection is comprised of a biofilm.

With respect to pulmonary infections, the compounds and compositions provided herein can be delivered to a patient in need of treated via an inhalation delivery device that provides local administration to the site of infection.

The inhalation delivery device employed in embodiments of the methods provided herein can be a nebulizer, dry powder inhaler (DPI), or a metered dose inhaler (MDI), or any other suitable inhalation delivery device known to one of ordinary skill in the art. The device can contain and be used to deliver a single dose of the composition or the device can contain and be used to deliver multi-doses of the composition of the present invention.

According to one embodiment, a dry powder particulate composition is delivered to a patient in need thereof via a metered dose inhaler (MDI), dry powder inhaler (DPI), atomizer, nebulizer or liquid dose instillation (LDI) technique to provide for glycopeptide delivery. With respect to inhalation therapies, those skilled in the art will appreciate that where a hollow and porous microparticle composition is employed, the composition is particularly amenable for delivery via a DPI. Conventional DPIs comprise powdered formulations and devices where a predetermined dose of medicament, either alone or in a blend with lactose earner particles, is delivered as an aerosol of dry powder for inhalation.

The medicament is formulated in a way such that it readily disperses into discrete particles with an MMD between 0.5 to 20 µm, for example from 0.5-5 µm, and are further characterized by an aerosol particle size distribution less than about 10 µm mass median aerodynamic diameter (MMAD), and in some embodiments, less than 5.0 µm. The MMAD of the powders will characteristically range from about 0.5-10 µm, from about 0.5-5.0 µm, or from about 0.5-4.0 µm.

The powder is actuated either by inspiration or by some external delivery force, such as pressurized air. Examples of DPIs suitable for administration of the particulate compositions of the present invention are disclosed in U.S. Pat. Nos. 5,740,794, 5,785,049, 5,673,686, and 4,995,385 and PCT application Nos. 00/72904, 00/21594, and 01/00263, the disclosure of each of which is incorporated by reference in their entireties for all purposes. DPI formulations are typically packaged in single dose units such as those disclosed in the aforementioned patents or they employ reservoir systems capable of metering multiple doses with manual transfer of the dose to the device.

The compositions disclosed herein may also be administered to the nasal or pulmonary air passages of a patient via aerosolization, such as with a metered dose inhaler (MDI). Breath activated MDIs are also compatible with the methods provided herein.

Along with the aforementioned embodiments, the compositions disclosed herein may be delivered to a patient in need thereof via a nebulizer, e.g., a nebulizer disclosed in PCT WO 99/16420, the disclosure of which is hereby incorporated in its entirety by reference, in order to provide an aerosolized medicament that may be administered to the pulmonary air passages of the patient. A nebulizer type inhalation delivery device can contain the compositions of the present invention as a solution, usually aqueous, or a suspension. For example, the prostacyclin compound or composition can be suspended in saline and loaded into the inhalation delivery device. In generating the nebulized spray of the compositions for inhalation, the nebulizer delivery device may be driven ultrasonically, by compressed air, by other gases, electronically or mechanically (e.g., vibrating mesh or aperture plate). Vibrating mesh nebulizers generate fine particle, low velocity aerosol, and nebulize therapeutic solutions and suspensions at a faster rate than conventional jet or ultrasonic nebulizers. Accordingly, the duration of treatment can be shortened with a vibrating mesh nebulizer, as compared to a jet or ultrasonic nebulizer. Vibrating mesh nebulizers amenable for use with the methods described herein include the Philips Respironics I-Neb®, the Omron MicroAir, the Nektar Aeroneb®, and the Pari eFlow®.

The nebulizer may be portable and hand held in design, and may be equipped with a self contained electrical unit. The nebulizer device may comprise a nozzle that has two coincident outlet channels of defined aperture size through which the liquid formulation can be accelerated. This results in impaction of the two streams and atomization of the formulation. The nebulizer may use a mechanical actuator to force the liquid formulation through a multiorifice nozzle of defined aperture size(s) to produce an aerosol of the formulation for inhalation. In the design of single dose nebulizers, blister packs containing single doses of the formulation may be employed.

In the present invention, the nebulizer may be employed to ensure the sizing of particles is optimal for positioning of the particle within, for example, the pulmonary membrane.

Upon nebulization, the nebulized composition (also referred to as "aerosolized composition") is in the form of aerosolized particles. The aerosolized composition can be characterized by the particle size of the aerosol, for example, by measuring the "mass median aerodynamic diameter" or "fine particle fraction" associated with the aerosolized composition. "Mass median aerodynamic diameter" or "MMAD" is normalized regarding the aerodynamic separation of aqua aerosol droplets and is determined by impactor measurements, e.g., the Andersen Cascade Impactor (ACI) or the Next Generation Impactor (NGI). The gas flow rate, in one embodiment, is 2example8 Liter per minute for the ACI and 15 liters per minute for the NGI.

"Geometric standard deviation" or "GSD" is a measure of the spread of an aerodynamic particle size distribution. Low GSDs characterize a narrow droplet size distribution (homogeneously sized droplets), which is advantageous for targeting aerosol to the respiratory system. The average droplet size of the nebulized composition provided herein, in one embodiment is less than 5 μm or about 1 μm to about 5 μm, and has a GSD in a range of 1.0 to 2.2, or about 1.0 to about 2.2, or 1.5 to 2.2, or about 1.5 to about 2.2.

"Fine particle fraction" or "FPF," as used herein, refers to the fraction of the aerosol having a particle size less than 5 μm in diameter, as measured by cascade impaction. FPF is usually expressed as a percentage.

In one embodiment, the mass median aerodynamic diameter (MMAD) of the nebulized composition is about 1 μm to about 5 μm, or about 1 μm to about 4 μm, or about 1 μm to about 3 μm or about 1 μm to about 2 μm, as measured by the Anderson Cascade Impactor (ACI) or Next Generation Impactor (NGI). In another embodiment, the MMAD of the nebulized composition is about 5 μm or less, about 4 μm or less, about 3 μm or less, about 2 μm or less, or about 1 μm or less, as measured by cascade impaction, for example, by the ACI or NGI.

In one embodiment, the MMAD of the aerosol of the pharmaceutical composition is less than about 4.9 μm, less than about 4.5 μm, less than about 4.3 μm, less than about 4.2 μm, less than about 4.1 μm, less than about 4.0 μm or less than about 3.5 μm, as measured by cascade impaction.

In one embodiment, the MMAD of the aerosol of the pharmaceutical composition is about 1.0 μm to about 5.0 μm, about 2.0 μm to about 4.5 μm, about 2.5 μm to about 4.0 μm, about 3.0 μm to about 4.0 μm or about 3.5 μm to about 4.5 μm, as measured by cascade impaction (e.g., by the ACI or NGI).

In one embodiment, the FPF of the aerosolized composition is greater than or equal to about 50%, as measured by the ACI or NGI, greater than or equal to about 60%, as measured by the ACI or NGI or greater than or equal to about 70%, as measured by the ACI or NGI. In another embodiment, the FPF of the aerosolized composition is about 50% to about 80%, or about 50% to about 70% or about 50% to about 60%, as measured by the NGI or ACI.

In one embodiment, a metered dose inhalator (MDI) is employed as the inhalation delivery device for the compositions of the present invention. In a further embodiment, the prostacyclin compound is suspended in a propellant (e.g., hydrofluorocarbon) prior to loading into the MDI. The basic structure of the MDI comprises a metering valve, an actuator and a container. A propellant is used to discharge the formulation from the device. The composition may consist of particles of a defined size suspended in the pressurized propellant(s) liquid, or the composition can be in a solution or suspension of pressurized liquid propellant(s). The propellants used are primarily atmospheric friendly hydrofluorocarbons (HFCs) such as 134a and 227. The device of the inhalation system may deliver a single dose via, e.g., a blister pack, or it may be multi dose in design. The pressurized metered dose inhalator of the inhalation system can be breath actuated to deliver an accurate dose of the lipid-containing formulation. To insure accuracy of dosing, the delivery of the formulation may be programmed via a microprocessor to occur at a certain point in the inhalation cycle. The MDI may be portable and hand held.

In one embodiment, a dry powder inhaler (DPI) is employed as the inhalation delivery device for the compositions of the present invention.

In one embodiment, the DPI generates particles having an MMAD of from about 1 μm to about 10 μm, or about 1 μm to about 9 μm, or about 1 μm to about 8 μm, or about 1 μm to about 7 μm, or about 1 μm to about 6 μm, or about 1 μm to about 5 μm, or about 1 μm to about 4 μm, or about 1 μm to about 3 μm, or about 1 μm to about 2 μm in diameter, as measured by the NGI or ACI. In another embodiment, the DPI generates particles having an MMAD of from about 1 μm to about 10 μm, or about 2 μm to about 10 μm, or about 3 μm to about 10 μm, or about 4 μm to about 10 μm, or about 5 μm to about 10 μm, or about 6 μm to about 10 μm, or about 7 μm to about 10 μm, or about 8 μm to about 10 μm, or about 9 μm to about 10 μm, as measured by the NGI or ACI.

In one embodiment, the MMAD of the particles generated by the DPI is about 1 μm or less, about 9 μm or less, about 8 μm or less, about 7 μm or less, 6 μm or less, 5 μm or less, about 4 μm or less, about 3 μm or less, about 2 μm or less, or about 1 μm or less, as measured by the NGI or ACI.

In one embodiment, each administration comprises 1 to 5 doses (puffs) from a DPI, for example, 1 dose (1 puff), 2 dose (2 puffs), 3 doses (3 puffs), 4 doses (4 puffs) or 5 doses (5 puffs). The DPI, in one embodiment, is small and transportable by the patient.

In one embodiment, the MMAD of the particles generated by the DPI is less than about 9.9 μm, less than about 9.5 μm, less than about 9.3 μm, less than about 9.2 μm, less than about 9.1 μm, less than about 9.0 μm, less than about 8.5 μm, less than about 8.3 μm, less than about 8.2 μm, less than about 8.1 μm, less than about 8.0 μm, less than about 7.5 μm, less than about 7.3 μm, less than about 7.2 μm, less than about 7.1 μm, less than about 7.0 μm, less than about 6.5 μm, less than about 6.3 μm, less than about 6.2 μm, less than about 6.1 μm, less than about 6.0 μm, less than about 5.5 μm, less than about 5.3 μm, less than about 5.2 μm, less than about 5.1 μm, less than about 5.0 μm, less than about 4.5 μm, less than about 4.3 μm, less than about 4.2 μm, less than about 4.1 μm, less than about 4.0 μm or less than about 3.5 μm, as measured by the NGI or ACI.

In one embodiment, the MMAD of the particles generated by the DPI is about 1.0 μm to about 10.0 μm, about 2.0 μm to about 9.5 μm, about 2.5 μm to about 9.0 μm, about 3.0 μm to about 9.0 μm, about 3.5 μm to about 8.5 μm or about 4.0 μm to about 8.0 μm.

In one embodiment, the FPF of the prostacyclin particulate composition generated by the DPI is greater than or equal to about 40%, as measured by the ACI or NGI, greater than or equal to about 50%, as measured by the ACI or NGI, greater than or equal to about 60%, as measured by the ACI or NGI, or greater than or equal to about 70%, as measured by the ACI or NGI. In another embodiment, the FPF of the aerosolized composition is about 40% to about 70%, or about 50% to about 70% or about 40% to about 60%, as measured by the NGI or ACI.

EXAMPLES

The present invention is further illustrated by reference to the following Examples. However, it is noted that these Examples, like the embodiments described above, are illustrative and are not to be construed as restricting the scope of the invention in any way.

Example 1—Synthesis of LGPC Derivatives

Lipo glycopeptide cleavable (LGPC) derivatives were prepared as follows.

Reductive Amination

To a reactor vessel equipped with temperature control and agitation was added anhydrous DMF and DIPEA. The resulting solution was heated to 65° C. with agitation and vancomycin HCl was added slowly in portions. Heating was continued until all of vancomycin HCl had dissolved (5-10 min).

The beige colored solution was allowed to cool to room temperature after which a solution of the desired aldehyde dissolved in DMF was added over 5-10 min. The resulting solution was allowed to stir overnight, typically producing a clear red-yellow solution. MeOH and TFA were introduced and stirring was further continued for at least 2 h. At the end of the stirring period, the imine forming reaction mixture was analyzed by HPLC which was characteristically typical. Borane tert-butylamine complex was added in portions and the reaction mixture was stirred at ambient temperature for an additional 2 h after which an in-process HPLC analysis of the reaction mixture indicated a near quantitative reduction of the intermediate imine group. After the reaction was over, the reaction mixture was purified using reverse phase C18 column chromatography (Phenomenex Luna 10 uM PREP C18(2) 250×21.2 mm column) using gradients of water and acetonitrile, each containing 0.1% (v/v) of TFA. Fractions were evaluated using HPLC and then pertinent fractions containing the target product were pooled together for the isolation of the product via lyophilization. Typical products were isolated as fluffy white solids. The procedure is shown at FIG. 1.

Aldehyde Preparation

Aldehydes used in the reductive amination reaction to form the LGPC can be prepared as set forth below and in Scheme 2.

To a reaction equipped with a stir bar was added an alcohol reagent containing an ester or amide bond and a suitable organic solvent (typically DCM or THF). The reaction mixture was stirred for approximately 5 min. to fully dissolve the starting material, at which point sodium bicarbonate and dess-martin periodinane were added to the reaction mixture. The reaction mixture was allowed to stir for 2 hours at which point TLC analysis was used to assess progress. In the instance that a large amount of unreacted starting material was present, an additional aliquot of dess-martin periodinane was added to the reaction mixture and progress was re-assessed after an additional 2 h of stirring. Once the reaction was complete, the reaction mixture was treated with DCM and a solution of 10% sodium thiosulfate saturated with $NaHCO_3$ for 90 min. The reaction mixture was then extracted with the sodium thiosulfate solutions (3×100 mL) and brine (2×100 mL) while retaining the organic layer. The organic layer was dried over $Na_2SO_4$, filtered, and solvent was removed under reduced pressure to yield the target aldehyde. The final material was typically used without further purification. However, in some instances, the aldehyde may be purified by either silica gel flash column chromatography or preparatory HPLC.

Cleavable Bond Formation (Ester and Amide Coupling Reactions)

Depending on the type of LGPC desired, one of the following coupling reactions is chosen to make the alcohol reactant for the aldehyde synthesis reaction.

Glycol+Acid chloride (Scheme 1). To a reaction vessel was added the appropriate glycol such as ethylene glycol and a suitable organic solvent such as THF or DCM. Temperature was adjusted to be 0° C. and stirring was initiated. Once the temperature stabilized, triethylamine was added in a single aliquot. Separately, a solution of the appropriate acid chloride such as decanoyl chloride and suitable organic solvent such as THF or DCM was prepared and charged into a dosing apparatus. The acid chloride solution was added drop wise over the course of few hours while stirring at 0° C. The reaction mixture was warmed to 25° C. over a 2 h period and the reaction mixture was allowed to stir for approximately 18 h at which point stirring was stopped. The reaction mixture was filtered to remove a white precipitate that had formed. Solvent was removed under reduced pressure to yield a thick, colorless oil.

The crude material was dissolved in EtOAc and washed with saturated $NaHCO_3$, and brine. The organic layer was dried over $Na_2SO_4$, filtered, and evaporated to dryness to yield crude product, typically as a white solid. The crude material was purified using prep-HPLC with a CN column and an isocratic method with 10% isopropyl alcohol as the mobile phase. Pure fractions were combined and solvent was removed to yield the target compound, typically as a white solid.

Scheme 1. Glycol + Acid chloride coupling reaction.

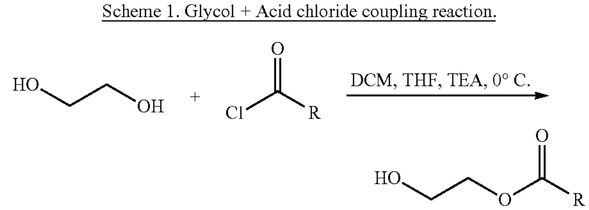

Glycol+Carboxylic Acid+Coupling Reagent (Scheme 2). To a clean vessel was added a suitable organic solvent (typically N,N-Dimethylformamide), DIPEA, the appropriate carboxylic acid such as decanoic acid, an coupling reagent such as HATU or PyBOP, and the appropriate glycol such as ethylene glycol. The vial was vortexed for 30 seconds to help dissolve the compounds. The reaction was allowed to shake overnight at 40° C. and ~125 rpm. Solvent was removed under reduced pressure and the crude reaction mixture was purified using silica gel flash column chromatography with a gradient method using hexanes, EtOAc, and IPA as the mobile phases. Pure fractions were combined and solvent was removed to yield the target compound, typically as a white solid.

Scheme 2. Glycol + Carboxylic Acid + Coupling Reagent coupling reaction.

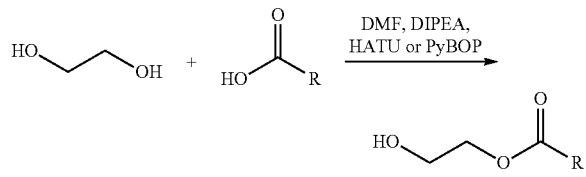

Hydroxy Alkyl Halide+Carboxylic Acid (Scheme 3). To a vial was added a suitable organic solvent such as N,N-Dimethylformamide, the appropriate acid chloride such as decanoyl chloride, and a hydroxyl alkyl halide such as 2-iodoethanol. The reaction mixture was then placed in an incubated shaker set at 40° C. and ~125 rpm where it was left to shake overnight. Solvent was removed under reduced pressure and the residue was subjected to liquid-liquid extraction using $H_2O$ (40 mL) and hexanes (3×75 ml). Organic layers were combined and solvent was removed under reduced pressure. The crude material was purified via silica gel flash column chromatography using a gradient method with hexanes and ethylacetate as the mobile phases. Fractions of interest were combined and solvent was removed under reduced pressure to produce the target compound, typically as a thick oil.

Scheme 3. Hydroxy Alkyl Halide + Carboxylic Acid coupling reaction.

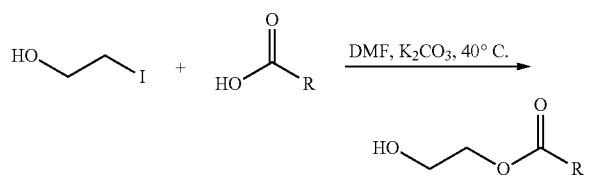

Alkyl Halide+Hydroxy Acid coupling reaction (Scheme 4). To a vial was added a suitable organic solvent such as N,N-Dimethylformamide, an appropriate hydroxyl acid such as glycolic acid, and an alkyl halide such as 1-Iodo-decane. The reaction mixture was then placed in an incubated shaker set at 40° C. and ~125 rpm where it was left to shake overnight. Solvent was removed under reduced pressure and the residue was subjected to liquid-liquid extraction using $H_2O$ (40 mL) and hexanes (3×75 ml). Organic layers were combined and solvent was removed under reduced pressure. The crude material was purified via silica gel flash column chromatography using a gradient method with hexanes and ethylacetate as the mobile phases. Fractions of interest were combined and solvent was removed under reduced pressure to produce the target compound, typically as a thick oil.

Scheme 4. Alkyl Halide + Hydroxy Acid coupling reaction.

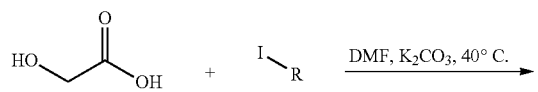

-continued

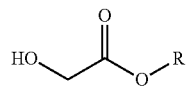

Amino alcohol+Acid Chloride (Scheme 5). To a reactor vessel was added the appropriate amino alcohol such as ethanolamine and a suitable organic solvent such as THF or DCM. Temperature was adjusted to be 0° C. and stirring was initiated. Once the temperature stabilized triethylamine was added in a single aliquot. Separately, a solution of the appropriate acid chloride such as decanoyl chloride and suitable organic solvent such as THF or DCM was prepared and charged into a dosing apparatus. The acid chloride solution was added drop wise over the course of few hours while stirring at 0° C. The reaction mixture was warmed to 25° C. over a 2 h period and the reaction mixture was allowed to stir for approximately 18 h at which point stirring was stopped. The reaction mixture was filtered to remove a white precipitate that had formed. Solvent was removed under reduced pressure to yield a thick, colorless oil. The crude material was dissolved in EtOAc and washed with 0.1M HCl, saturated $NaHCO_3$, and brine. The organic layer was dried over $Na_2SO_4$, filtered, and evaporated to dryness to yield crude product, typically as a white solid. The crude material was purified using prep-HPLC with a CN column and an isocratic method with 10% isopropyl alcohol as the mobile phase. Pure fractions were combined and solvent was removed to yield the target compound, typically as a white solid.

Scheme 5. Amino alcohol + Acid Chloride coupling reaction

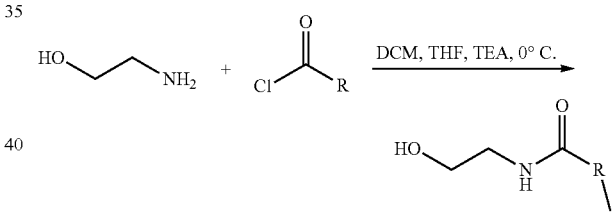

Amino alcohol+Carboxylic Acid+Coupling Reagent coupling reaction (Scheme 6). To a clean vessel was added a suitable organic solvent such as N,N-Dimethylformamide), DIPEA, the appropriate carboxylic acid such as decanoic acid, a coupling reagent such as HATU or PyBOP, and the appropriate amino alcohol such as ethanolamine. The vial was vortexed for 30 seconds to help dissolve the compounds. The reaction was allowed to shake overnight at 40° C. and ~125 rpm. Solvent was removed under reduced pressure and the crude reaction mixture was purified using silica gel flash column chromatography with a gradient method using hexanes, EtOAc, and IPA as the mobile phases. Pure fractions were combined and solvent was removed to yield the target compound, typically as a white solid.

Scheme 6. Amino alcohol + Carboxylic Acid + Coupling Reagent coupling reaction.

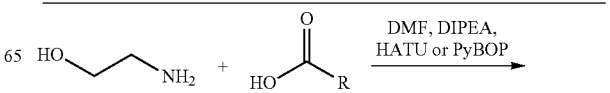

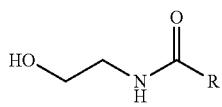

Alkyl amine+Hydroxy Acid+Coupling Reagent coupling reaction (Scheme 7). To a clean vessel was added a suitable organic solvent such as N,N-Dimethylformamide), DIPEA, the appropriate hydroxy acid such as glycolic acid, a coupling reagent such as HATU or PyBOP, and the appropriate alkyl amine such 1-aminodecane. The vial was vortexed for 30 s to help dissolve the compounds. The reaction was allowed to shake overnight at 40° C. and ~125 rpm. Solvent was removed under reduced pressure and the crude reaction mixture was purified using silica gel flash column chromatography with a gradient method using hexanes, EtOAc, and IPA as the mobile phases. Pure fractions were combined and solvent was removed to yield the target compound, typically as a white solid.

Scheme 7. Alkyl amine + Hydroxy Acid + Coupling Reagent coupling reaction

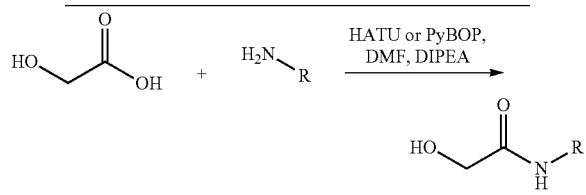

Example 2—Synthesis of LGPC Derivative RV65

Ester Bond Coupling (Scheme 8).

Scheme 8. Coupling reaction for RV65.

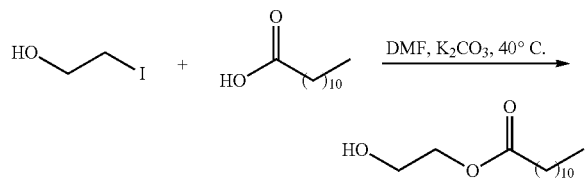

To a clean 20 mL scintillation vial was added N,N-Dimethylformamide (5 mL, Potassium Carbonate (0.862 g, 6.24 mmol), Laurie acid (0.5 g, 2.5 mmol), and 2-iodoethanol (0.43 g, 0.20 mL, 2.5 mmol). The reaction mixture was then placed in an incubated shaker set at 40° C. and –125 rpm where it was left to shake overnight. Solvent was removed under reduced pressure and the residue was subjected to liquid-liquid extraction using H$_2$O (40 mL) and hexanes (3×75 ml). Organic layers were combined and solvent was removed under reduced pressure. The crude material was purified via silica gel flash column chromatography using a gradient method with hexanes and ethyl acetate as the mobile phases. Fractions of interest were combined and solvent was removed under reduced pressure to produce the target compound (91.9 mg, 0.38 mmol) as a thick, slightly yellow-tinged oil.

Oxidation to Aldehyde

Scheme 9. Aldehyde synthesis.

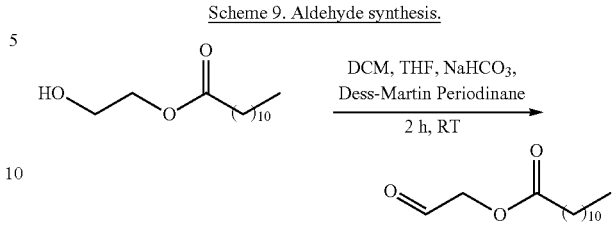

To a 20 mL scintillation vial was added 2-hydroxyethyl dodecanoate (0.184 g, 0.753 mmol), dess-martin periodinane (0.639 g, 1.506 mmol), and (SI) Dichloromethane (3.68 mL). The mixture was allowed to stir overnight and reaction progress was monitored via TLC. To the reaction mixture was added 2 mL of sodium thiosulfate (10% in water) and 2 mL of saturated sodium bicarbonate at the same time; at which point a white precipitate formed, the solution turned pink, and a small amount of bubbles were formed. The aqueous layer was washed with DCM (3×25 mL) at which point organic layers were combined, washed with brined, dried over Na$_2$SO$_4$, and filtered. The crude sample was evaporated to dryness under reduced pressure to produce 2-oxoethyl dodecanoate (0.26 g, 1.08 mmol) as a slightly pink-tinged solid. The final material was analyzed by TLC using a 2,4-DNP stain to reveal the presence of an aldehyde.

Reductive Amination

To a 40 mL vial equipped a stir bar was added anhydrous DMF (20 mL) and DIPEA (0.24 mL). The resulting solution was heated to 65° C. on an incubated shaker and vancomycin HCl (1.0 g, 0.7 mmol) was added slowly in portions. Heating was continued until all of vancomycin HCl had dissolved (5-10 min). The beige colored solution was allowed to cool to room temperature after which a solution of 2-oxoethyl dodecanoate (250 mg, 1.03 mmol) and DMF (5 mL) was added over 5-10 min. The resulting solution was allowed to stir overnight to give a clear red-yellow solution. MeOH (10 mL) and TFA (0.21 mL, 2.8 mmol) were introduced to the reaction mixture producing a small amount of white smoke; the reaction mixture also turned yellow. Stirring was further continued for at least 2 h. At the end of the stirring period, the imine forming reaction mixture was analyzed by HPLC which was characteristically typical. Borane tert-butylamine complex (60 mg, 0.7 mmol) was added in portions and the reaction mixture was stirred at ambient temperature for an additional 2 h after which an in-process HPLC analysis of the reaction mixture indicated a near quantitative reduction of the intermediate imine group. After the reaction was over the reaction mixture is purified using reverse phase C18 column chromatography (Phenomenex Luna 10 uM PREP C18(2) 250×21.2 mm column) using gradients of water and acetonitrile, each containing 0.1% (v/v) of TFA. Fractions were evaluated using HPLC and then pertinent fractions containing RV65 were pooled together for the isolation of the product via lyophilization. The target compound, RV65 (150 mg, 0.09 mmol, 13% overall yield), was obtained as a white solid in >97% purity (by HPLC).

Scheme 10. Synthesis of RV65.

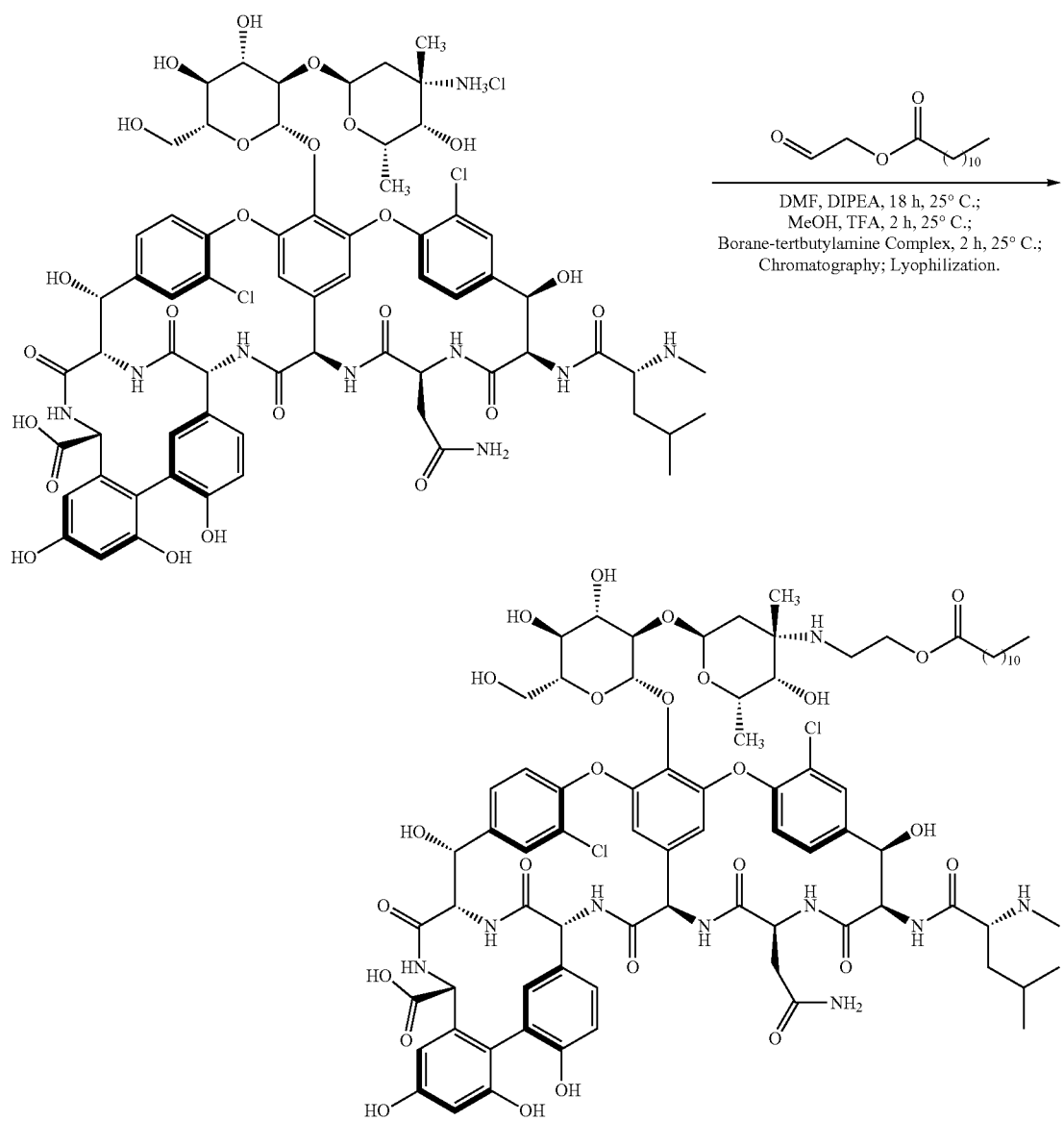

Example 3—Synthesis of LGPC Derivative RV62

Coupling (Scheme 11).

Scheme 11. Coupling reaction for RV62.

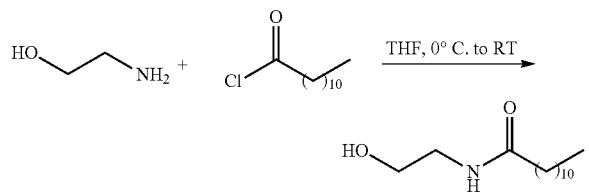

To a 400 mL reactor vessel equipped with pH monitoring, stirring, temperature control, inert gas, and a dosing apparatus was set up. To the reactor was added ethanolamine (3.461 g, 3.42 mL, 56.66 mmol, 2.1 equiv.) and THF (150 mL, 0.18 M, 25.412 Vols). The temperature was adjusted to be 0° C., stirring was initiated at 500 rpm, and pH monitoring was initiated. Once the temperature stabilized Triethylamine (4.095 g, 5.641 mL, 40.472 mmol, 1.5 equiv.) was added in a single aliquot. Separately, a solution of dodecanoyl chloride (5.903 g, 6.423 mL, 26.981 mmol, 1 equiv.) and THF (50 mL, 0.54 M, 8.471 Vols) was prepared and used to fill the dosing apparatus. The dodecanoyl chloride solution was added drop wise over the course of 5 h while controlling the temperature at 0° C. and the pH to basic conditions. The reaction mixture temperature was warmed to 25° C. over a 2 h period and the reaction mixture was allowed to stir for approximately 18 h at which point stirring was stopped. The reaction mixture was filtered to remove a white precipitate that had formed. Solvent was removed under reduced pressure to yield a thick, colorless oil. The crude material was dissolved in EtOAc (300 mL) and was washed with 0.1M HCl (3×100 mL), saturated NaHCO₃ (3×100 mL), and brine (3×100 mL). The organic layer was dried over Na$_2$SO$_4$, filtered, and evaporated to dryness to yield 4.45 g of crude product as a white solid. The crude material was purified using prep-HPLC with a CN column and an isocratic method with 10% isopropyl alcohol as the mobile phase. Pure fractions were combined and solvent was removed to yield the target compound as a white solid (3.15 g, 12.94 mmol, 48% yield).

Oxidation to Aldehyde

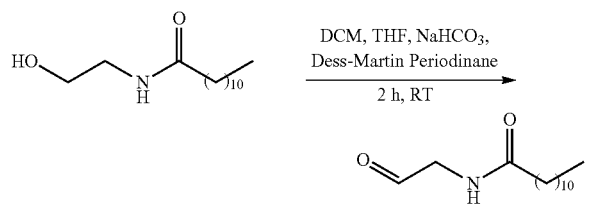

Scheme 12. Oxidation reaction for RV62 reactant.

To a 40 mL vial equipped with a stir bar was added N-(2-hydroxyethyl)decanamide (1 g, 4.109 mmol, 1 equiv.), dichloromethane (20 mL, 0.205 M, 20 Vols), and THF (10 mL, 0.411 M, 10 Vols). The reaction mixture was stirred for approximately 5 min. to fully dissolve the starting material at which point NaHCO$_3$ (0.69 g, 8.217 mmol, 2 equiv.) and dess-martin periodinane (2.178 g, 5.136 mmol, 1.25 equiv.) were added to the reaction mixture. The reaction mixture was allowed to stir for 2 h at which point TLC analysis indicated the reaction had reached completion. The reaction mixture was then treated with and a solution of 10% sodium thiosulfate saturated with NaHCO$_3$ for 90 min. The reaction mixture was then extracted with the sodium thiosulfate solutions (3×100 mL) and brine (2×100 mL) while retaining the organic layer. The organic layer (DCM) was dried over Na$_2$SO$_4$, filtered, and solvent was removed under reduced pressure to yield 673.1 mg (2.79 mmol, 68.9% yield) of the target compound a white solid that was used without further purification.

Reductive Amination

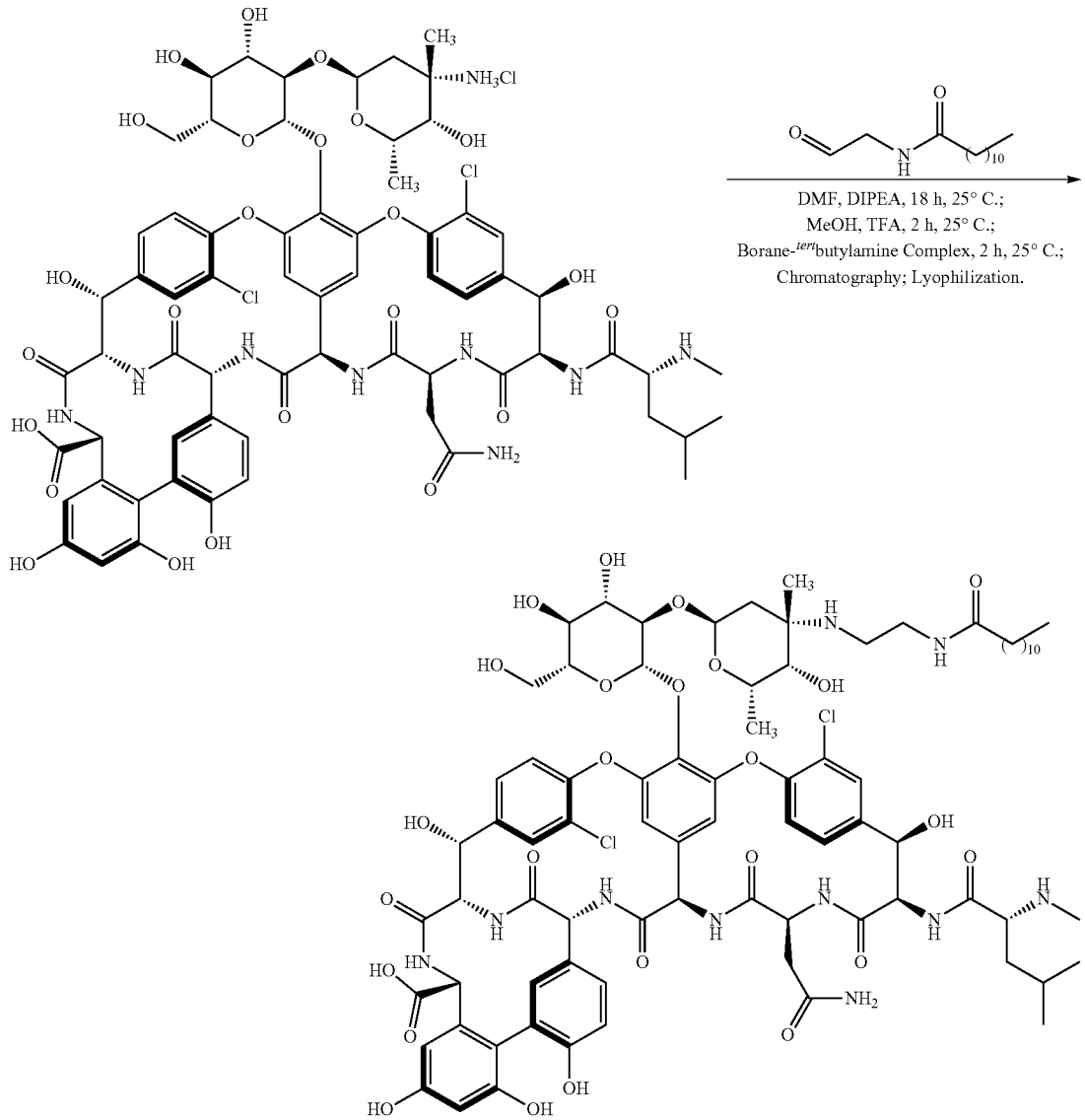

Scheme 13. Synthesis of RV62.

To a 400 mL reactor vessel equipped with pH monitoring, overhead stirring, temperature control, inert gas, and a dosing apparatus was prepared. To the reactor was added anhydrous DMF (50 mL) and DIPEA (0.694 mL). The resulting solution was heated to 65° C. with stirring and vancomycin HCl (2.9 g, 2.0 mmol) was added slowly in portions. Heating was continued until all of vancomycin HCl had dissolved (5-10 min). The beige colored solution was allowed to cool to 30° C. after which a solution of N-(2-oxoethyl)dodecanamide (673 mg, 2.8 mmol) and DMF was added over 5-10 min. The resulting solution was allowed to stir overnight to give a clear red-yellow solution. MeOH (25 mL) and TFA (0.61 mL, 8 mmol) were introduced and stirring was further continued for at least 2 h. At the end of the stirring period, the imine forming reaction mixture was analyzed by HPLC which was characteristically typical. Borane tert-butylamine complex (173 mg, 2.0 mmol) was added in portions and the reaction mixture was stirred at ambient temperature for an additional 2 h after which an in-process HPLC analysis of the reaction mixture indicated a near quantitative reduction of the intermediate imine group. After the reaction was over the reaction mixture is purified using reverse phase C18 column chromatography (Phenomenex Luna 10 uM PREP C18(2) 250×21.2 mm column) using gradients of water and acetonitrile, each containing 0.1% (v/v) of TFA. Fractions were evaluated using HPLC and then pertinent fractions containing RV62 were pooled together for the isolation of the product via lyophilization. The target compound, RV62 (600 mg, 0.35 mmol, 18% overall yield), was obtained as a white solid in >97% purity (by HPLC).

Example 4—Synthesis of LGPC Chloroeremomycin Derivative

To a 20 mL scintillation vial equipped with a stir bar was added chloroeremomycin and a solution of copper (II) acetate in MeOH. The reaction mixture was stirred at room temperature until the chloroeremomycin had dissolved. To the reaction mixture was then added the appropriate aldehyde and sodium cyanoborohydride as a 1M solution in THF. The reaction mixture was transferred to an incubated shaker set to 45° C. and reaction progress was monitored by HPLC. In some instances, it was necessary to add an additional aliquot of aldehyde reagent. The reaction mixture was allowed to shake overnight at 45° C. The reaction mixture was cooled to RT and sodium borohydride was added to convert residual aldehyde reagent to the corresponding alcohol. The pH was adjusted to between 7-8 using either acetic acid or 0.1M NaOH and volatile solvents were removed by blowing $N_2(g)$ with gentle heat. To the reaction mixture was added acetonitrile to precipitate the crude product as an off-white solid. The reaction mixture was centrifuged and the liquid was decanted. The solid was dissolved in 10% $MeCN/H_2O$ containing 0.1% phosphoric acid to decomplex the copper at which point the solution briefly turned purple and then took on a yellow tinge. Preparatory HPLC was used to purify final product and LCMS was used to confirm compound identity and purity.

A diagram of the reaction is provided below as scheme 14.

Scheme 14. Synthesis of LGPC chloroeremomycin derivative.

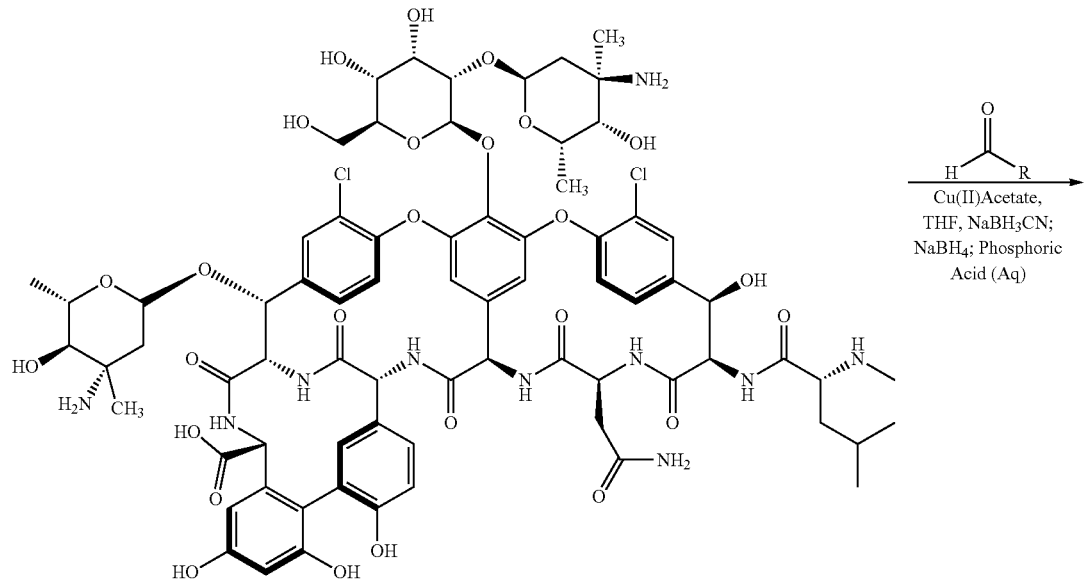

-continued

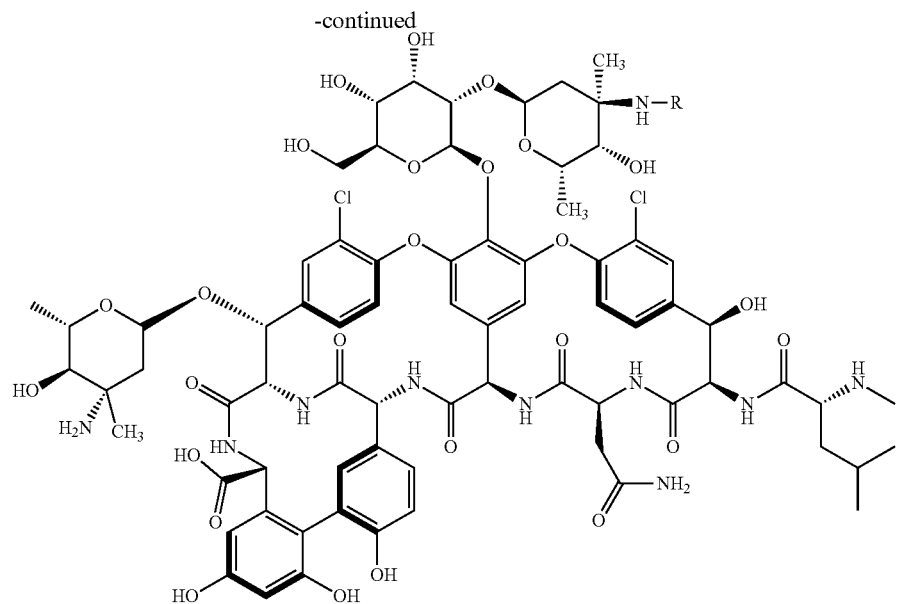

Example 5—C-Terminus Modification of LGPC Derivative

To a round bottom flask equipped with a stir bar was added a LPGC derivative, a 1:1 solution of DMF:DMSO, and DIPEA. To the reaction mixture was then added HBTU and the appropriate amine (e.g., 3-(dimethylamino)-1-propylamine). Reaction progress was monitored by HPLC. Once complete, the reaction was quenched upon addition of 1:1 $H_2O$:MeOH. The crude material was then purified using reverse phase C18 preparatory HPLC. Purified fractions were lyophilized to yield the target products, typically as a white fluffy powder in modest yield and high purity.

Example 6—Resorcinol-Like Modification of LGPC Derivative

To a round bottom flask equipped with a stir bar was added (Aminomethyl)phosphoric acid, water, and DIPEA. The reaction mixture was allowed to stir for 15 minutes at room temperature. To the reaction mixture was then added acetonitrile and formaldehyde, 37% solution in $H_2O$. The reaction mixture was allowed to stir for an additional 15 min. at which point a LGPC derivative and additional DIPEA were added. Reaction progress was closely monitored using HPLC. Once complete the reaction mixture was purified using reverse phase C18 preparative HPLC. Purified fractions were lyophilized to yield the target product as a white fluffy powder.

Example 7—Minimum Inhibitory Concentration (MIC) of Compounds of Formula (II)

Compounds of the invention were evaluated for their ability to inhibit bacterial growth in two MRSA strains—MRSA 1556 and MRSA 29213. The minimal inhibitory concentrations MICs are summarized in Table 1. Table 2 provides MIC concentrations for metabolites of the ester and amide compounds, RV80 (metabolite of RV65 ester) and RV82 (metabolite of RV62 amide). MIC values for vancomycin and telavancin are also provided.

MIC Testing: Glycopeptide compounds were dissolved in 100% DMSO. In vitro activities were determined using CLSI-guided broth susceptibility testing to measure drug minimum inhibitory concentrations (MICs) of the compounds against the quality control strain ATCC 29213 (MSSA) and the MRSA isolate ATCC BAA-1556.

TABLE 1

| Compound | Class | MIC Values, µg/mL MRSA 1556 | MSSA 29213 | $R^1$ | $R^2$ | $R^3$ | $R^4$ |
|---|---|---|---|---|---|---|---|
| RV90 | Ester | 0.250 | 0.250 | —$(CH_2)_2$—O—C(O)—$(CH_2)_6$—$CH_3$ | OH | H | H |
| RV67 | Ester | 0.157 | 0.094 | —$(CH_2)_2$—O—C(O)—$(CH_2)_7$—$CH_3$ | OH | H | H |
| RV54 | Ester | 0.167 | 0.146 | —$(CH_2)_2$—O—C(O)—$(CH_2)_8$—$CH_3$ | OH | H | H |
| RV66 | Ester | 0.125 | 0.125 | —$(CH_2)_2$—O—C(O)—$(CH_2)_9$—$CH_3$ | OH | H | H |
| RV65 | Ester | 0.094 | 0.063 | —$(CH_2)_2$—O—C(O)—$(CH_2)_{10}$—$CH_3$ | OH | H | H |

TABLE 1-continued

| Compound | Class | MIC Values, μg/mL | | R¹ | R² | R³ | R⁴ |
|---|---|---|---|---|---|---|---|
| | | MRSA 1556 | MSSA 29213 | | | | |
| RV88 | Ester | 0.125 | 0.125 | —(CH$_2$)$_2$—O—C(O)—(CH$_2$)$_{12}$—CH$_3$ | OH | H | H |
| RV89 | Ester | 1.000 | 0.500 | —(CH$_2$)$_2$—O—C(O)—(CH$_2$)$_{14}$—CH$_3$ | OH | H | H |
| RV55 | Ester | 0.250 | 0.250 | —(CH$_2$)$_3$—O—C(O)—(CH$_2$)$_9$—CH$_3$ | OH | H | H |
| RV93 | Amide | 0.125 | 0.125 | —(CH$_2$)$_2$—NH—C(O)—(CH$_2$)$_6$—CH$_3$ | OH | H | H |
| RV60 | Amide | 0.063 | 0.063 | —(CH$_2$)$_2$—NH—C(O)—(CH$_2$)$_7$—CH$_3$ | OH | H | H |
| RV56 | Amide | 0.063 | 0.063 | —(CH$_2$)$_2$—NH—C(O)—(CH$_2$)$_8$—CH$_3$ | OH | H | H |
| RV61 | Amide | 0.031 | 0.031 | —(CH$_2$)$_2$—NH—C(O)—(CH$_2$)$_9$—CH$_3$ | OH | H | H |
| RV62 | Amide | 0.023 | 0.023 | —(CH$_2$)$_2$—NH—C(O)—(CH$_2$)$_{10}$—CH$_3$ | OH | H | H |
| RV92 | Amide | 0.031 | 0.023 | —(CH$_2$)$_2$—NH—C(O)—(CH$_2$)$_2$—CH$_3$ | OH | H | H |
| RV91 | Amide | 0.250 | 0.188 | —(CH$_2$)$_2$—NH—C(O)—(CH$_2$)$_{14}$—CH$_3$ | OH | H | H |
| RV94 | Amide | 0.031 | 0.031 | —CH$_2$—C(O)—NH—(CH$_2$)$_9$—CH$_3$ | OH | H | H |
| RV95 | Amide | 0.031 | 0.031 | —CH$_2$—C(O)—NH—(CH$_2$)$_{11}$—CH$_3$ | OH | H | H |
| RV72 | Amide | 0.5 | 0.5 | —(CH$_2$)$_2$—NH—C(O)—(CH$_2$)$_9$—CH$_3$ | NH—(CH$_2$)$_3$—N(CH$_3$)$_2$ | H | H |
| RV73 | Amide | 0.5 | 0.5 | —(CH$_2$)$_2$—NH—C(O)—(CH$_2$)$_9$—CH$_3$ | OH | H | CH$_2$—NH—CH$_2$—PO$_3$H$_2$ |

TABLE 2

| Compound | MIC Values, μg/mL | |
|---|---|---|
| | MRSA 1556 | MSSA 29213 |
| Vancomycin | 1 | 1 |
| Telavancin | 0.063 | 0.063 |
| RV80 | 1 | 1 |
| RV82 | 3 | 3 |

MIC values for amide derivatives were lower than the ester derivatives (Table 1). RV62 was found to be about 3×more efficacious than RV65, the ester with the lowest measured MIC.

Example 8—Degradation of RV62 and RV65

RV62 and RV65 degradation was determined according to the following procedures.

Compounds were dissolved and diluted with 1 mM Tris buffer (pH 6.99) to achieve a concentration of 54 μg/mL (stock solution). 0.5 mL of stock solution was further diluted with acetonitrile to a total volume of 10 mL. The stock solution was incubated at 40° C., with samples withdrawn at 3, 6, 24, and 72 h and tested by HPLC.

HPLC method: Samples were injected onto a 100×2.1 mm Waters Cortecs HILIC with a particle size of 1.6 μm. The mobile phase consisted of water (0.1% formic acid) and acetonitrile (0.1% formic acid). The analytic method utilized a gradient from 10% water (0.1% formic acid)/90% acetonitrile (0.1% formic acid) to 70% water (0.1% formic acid)/30% acetonitrile (0.1% formic acid). The HPLC instrument was equipped with a UV detector (280 nm). Compounds were identified by mass.

Figure 3:
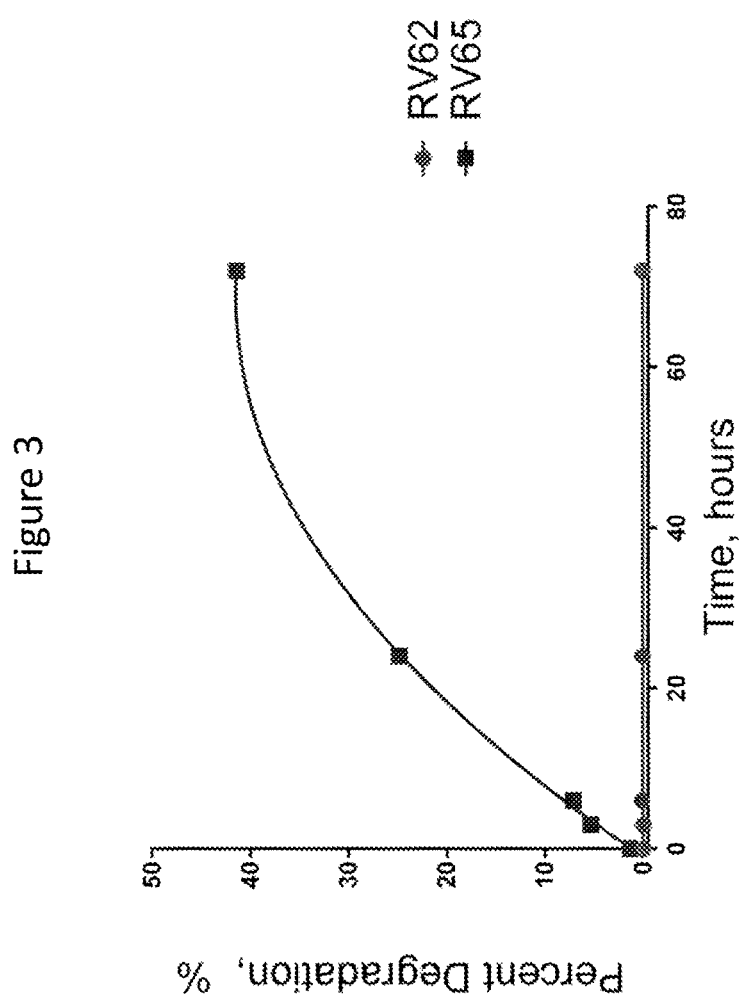
FIG. 3 is a graph of the percent degradation of RV62 and RV65 as a function of time, as determined by HPLC.

FIG. 3 shows the extent of hydrolysis of RV62 and RV65 at 3, 6, 24, and 72 h. The amount of cleaved glycopeptide was found to increase steadily up to the 24 h time point for RV65. For RV65, between 24 and 72 h, the rate of cleavage appears to plateau, such that at 72 h, the peak area for the cleaved glycopeptide was determined to be about 42% of the total.

Example 9—Enzyme Mediated Hydrolysis of LGPC Glycopeptide Ester Derivatives

The respective LGPC was dissolved in propanol:TBA:H2O (1:1:1) at ~3 mg/mL, with DSPE-PEG2000 (~1.5 mg/mL), and lactosedeucine (7:3 at ~20 mg/mL). The solution was flash frozen and lyophilized. The lyophilized cake was suspended in PBS (pH=8.0) at 2 mg/mL LGPC. The LGPC was suspended at 0.5-1 mg/mL in PBS (pH adjusted to 8.0 with NaOH) and placed at 37° C. in the presence and absence of esterase (0.2 U/mL). Aliquots were removed at preselected time intervals of 0, 15, 30, 45, 60, 90 and 120 min. Aliquots (125 μL) were diluted in 500 μL 1:1 acetonitrile (ACN):H$_2$O with 0.1% formic acid to stop enzymatic degradation. Diluted samples were analyzed by HPLC to determine the relative peak area for the parent and the metabolite for each LGPC tested.

Figure 4:
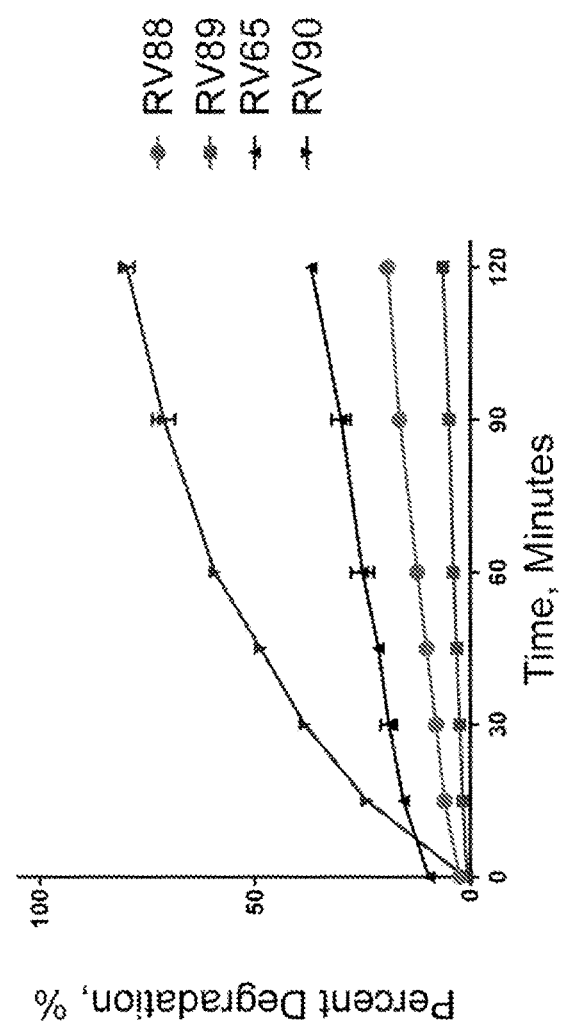
FIG. 4 is a graph of the percent degradation of certain LGPC derivatives (RV65, RV88, RV89, RV90), after incubation with esterase, as determined by HPLC.

FIG. 4 is a graph of percent LGPC degradation as a function of time. Esterase mediated hydrolysis of ester LGPC derivatives is chain length dependent.

Example 10—Metabolism of RV62 and RV65 in Rat Plasma

RV62 and RV65 were dissolved in 100% DMSO. Stock solutions were diluted using rat plasma to contain less than 1% organic solvent with a final drug concentration of 50 μg/mL. Samples were briefly vortexed and then incubated in a shaker set to 37° C. and 300 rpm. Aliquots were removed at specified time points and store at −80° C. until extraction and analysis. Samples were extracted using a solution of 10% TCA and analyzed using LCMS.

Figure 5:
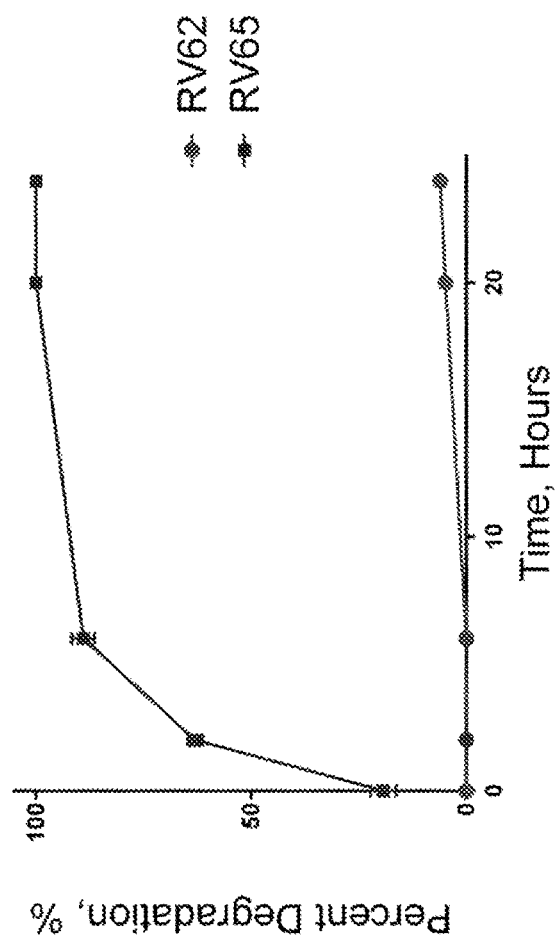
FIG. 5 is a graph showing the hydrolysis of RV62 and RV65 as a function of time, after incubation in rat plasma over 24 h.

The hydrolysis of amide RV62 and ester RV65 incubated in rat plasma was determined (FIG. 5). That data shows that RV65 (ester) was metabolized faster in plasma compared to RV62 (amide). For RV65, ~90% of degradant (RV80) was detected in plasma after only 6 h incubation. In contrast, only 6% of degradant of RV62 (RV82) was detected in plasma even after 24 h incubation. As such, under the test conditions, the ester moiety was found to be more labile than the corresponding amide moiety.

Example 11—Pharmacokinetics (PK) of RV62 and its Hydrolysis Product RV82, Given by Nose Only Inhalation in Rats The structures are RV62 and RV82 are provided below.

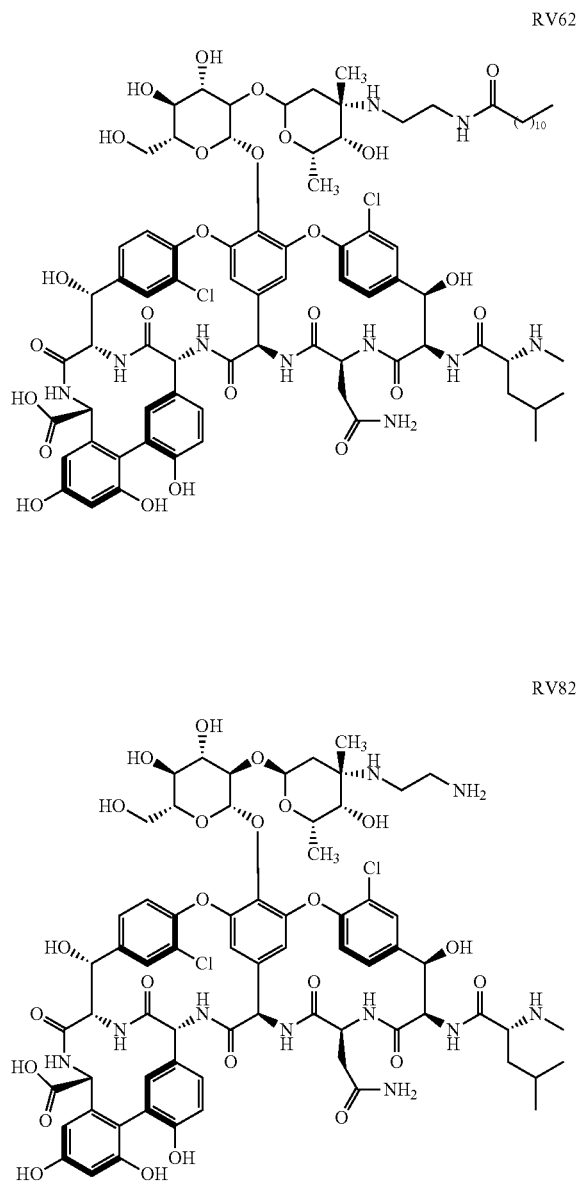

Male Sprague-Dawley rats from Charles River Laboratories weighing between 250 g and 300 g at the start of dosing were used in the study.

RV62 solution 5 mg/mL in Bicine buffer 0.8 mg/mL at pH 9.5 was prepared prior to animal dosing. RV62 was administered using Aeroneb nebulizer (Aerogen) which delivers a mass mean aerosol diameter between 2.5 to 4 μm and a range of 0.2-0.4 mL/min of nebulization rate. The volume of material to be nebulized was 6 mL, and the total administration time was ~20 min.

On the day of dosing, the eleven rats were placed into the nose-cone restraint chambers which are connected to a 12-port nose-only inhalation chamber (CH Technologies). The test article was delivered from the nebulizer to the chamber with an airflow of 6 L/min. At the end of the compound exposure, the rats were either returned to their cage or sacrificed at 0.5 h after the end of nebulization which was defined as the immediately post dose (IPD) collection.

Figure 6:
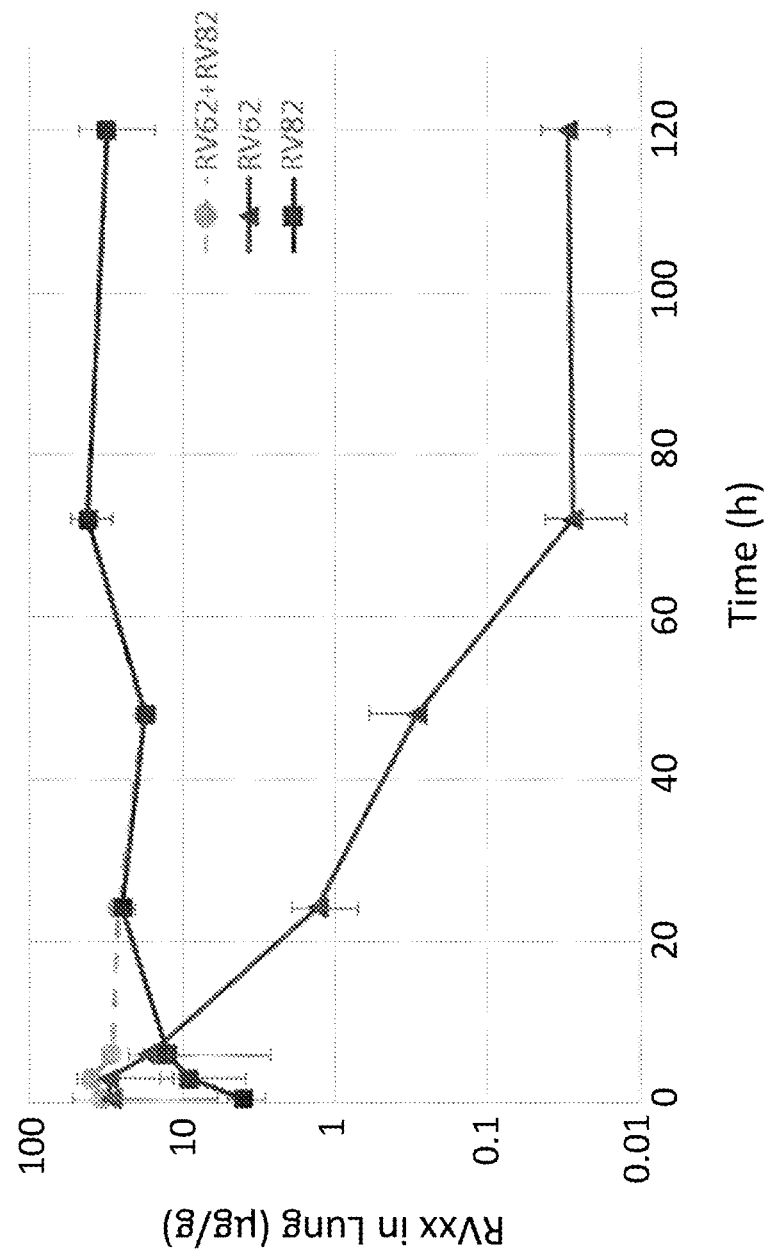
FIG. 6 is a graph showing the levels of RV62 (µg/g) and RV82 (µg/g) in the lung as a function of time.
Figure 7:
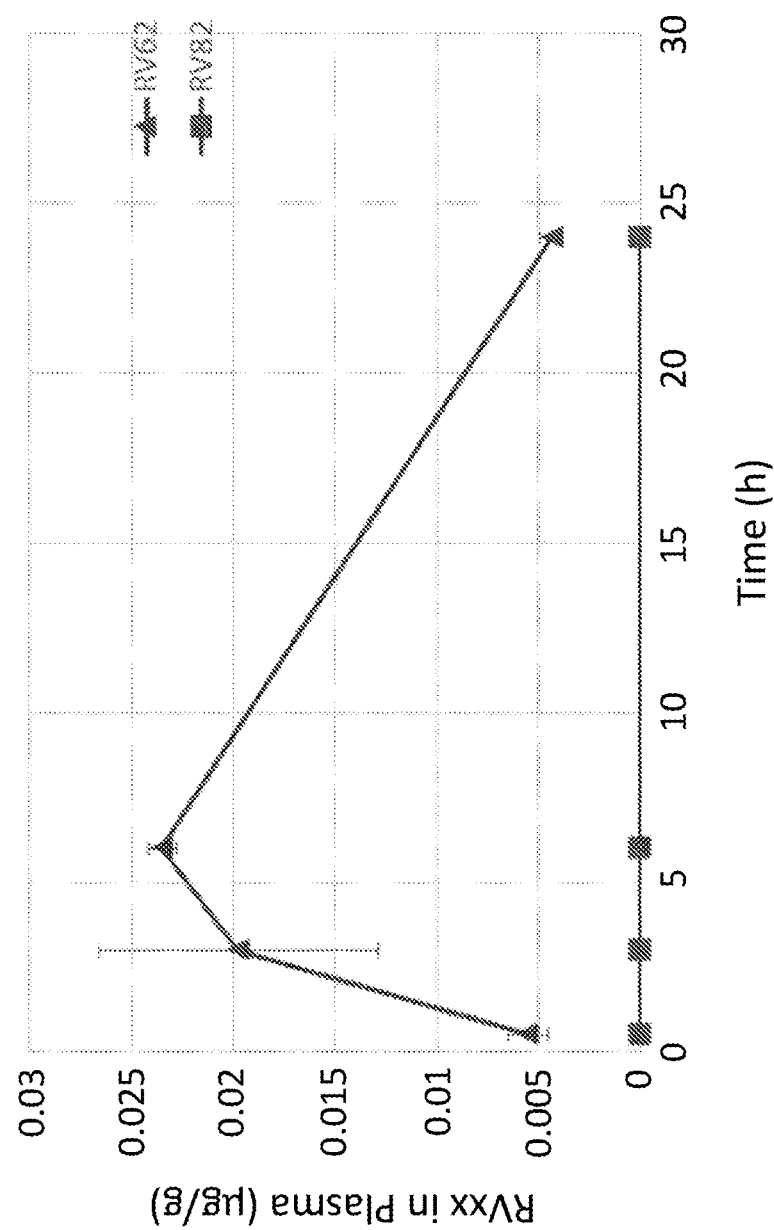
FIG. 7 is a graph showing the levels of RV62 (µg/g) and RV82 (µg/g) in blood plasma as a function of time.

For the terminal time points, rats were anesthetized with 2% isoflurane inhaled with pure oxygen and blood samples of 2.0 mL were obtained by heart puncture and transferred into a 2.0 mL K2-EDTA tube. The tubes were centrifuged at 4° C. to separate the plasma and aliquoted into three conical tubes and stored at −50° C. Lungs were extracted, weighed, and stored at −50° C. for subsequent analysis of lung drug concentrations. RV62 and RV82 were measured in both blood plasma and the lung by LC-MS/MS method. Results of the study are provided at FIG. 6 (lung) and FIG. 7 (blood plasma).

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method for treating a Gram positive pulmonary bacterial infection in a patient in need thereof, the method comprising:
    administering to the lungs of the patient via a nebulizer, dry powder inhaler (DPI) or metered dose inhaler (MDI), a composition comprising an effective amount of a compound of Formula (II), or a pharmaceutically acceptable salt thereof:

(II)

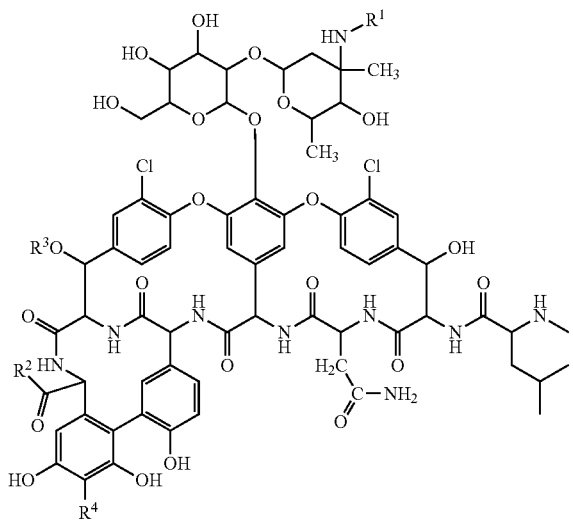

wherein,
R$^1$ is —(CH$_2$)$_{n1}$—C(O)—NH—(CH$_2$)$_{n2}$—CH$_3$; —(CH$_2$)$_{n1}$—NH—C(O)—(CH$_2$)$_{n2}$—CH$_3$; or —(CH$_2$)$_{n1}$—O—C(O)—(CH$_2$)$_{n2}$—CH$_3$;
n1 is 1, 2, 3, 4 or 5;
n2 is 6, 7, 8, 9, 10, 11, 12, 13, 14 or 15;
R$^2$ is OH or NH—(CH$_2$)$_q$—R$^5$;
q is 1, 2, 3, 4, or 5;
R$^3$ is H or

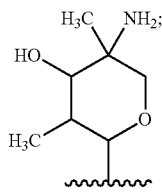

R$^4$ is H or CH$_2$—NH—CH$_2$—PO$_3$H$_2$; and
R$^5$ is —N(CH$_3$)$_2$, —N$^+$(CH$_3$)$_3$, —N$^+$(CH$_3$)$_2$(n-C$_{14}$H$_{29}$), or

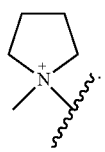

2. The method of claim 1, wherein R$^1$ is —(CH$_2$)$_{n1}$—NH—C(O)—(CH$_2$)$_{n2}$—CH$_3$ or —(CH$_2$)$_{n1}$—O—C(O)—(CH$_2$)$_{n2}$—CH$_3$.

3. The method of claim 1, wherein R$^1$ is —(CH$_2$)$_{n1}$—O—C(O)—(CH$_2$)$_{n2}$—CH$_3$.

4. The method of claim 1, wherein R$^1$ is —(CH$_2$)$_{n1}$—NH—C(O)—(CH$_2$)$_{n2}$—CH$_3$.

5. The method of claim 1, wherein R$^1$ is —(CH$_2$)$_{n1}$—C(O)—NH—(CH$_2$)$_{n2}$—CH$_3$.

6. The method of claim 5, wherein n1 is 1.

7. The method of claim 5, wherein n2 is 9, 10, 11, 12, 13, 14.

8. The method of claim 6, wherein n2 is 9, 10, 11, 12 or 13.

9. The method of claim 1, wherein R$^1$ is —(CH$_2$)$_{n1}$—C(O)—NH—(CH$_2$)$_{n2}$—CH$_3$, R$^2$ is OH, R$^3$ is H, R$^4$ is H, n1 is 1 and n2 is 9.

10. The method of claim 1, wherein the administering is carried out via a dry powder inhaler.

11. The method of claim 1, wherein the Gram-positive pulmonary bacterial infection is a Gram-positive pulmonary cocci infection.

12. The method of claim 11, wherein the Gram-positive pulmonary cocci infection is a *Staphylococcus* pulmonary infection.

13. The method of claim 11, wherein the Gram-positive pulmonary cocci infection is an *Enterococcus* pulmonary infection.

14. The method of claim 11, wherein the Gram-positive pulmonary cocci infection is a *Streptococcus* pulmonary infection.

15. The method of claim 12, wherein the *Staphylococcus* pulmonary infection is a *Staphylococcus aureus* (*S. aureus*) pulmonary infection.

16. The method of claim 15, wherein the *S. aureus* pulmonary infection is a methicillin-resistant *S. aureus* (MRSA) pulmonary infection.

17. The method of claim 1, wherein the patient is a cystic fibrosis patient.

18. The method of claim 4, wherein n1 is 2.

19. The method of claim 18, wherein n2 is 10.

20. The method of claim 1, wherein R$^1$ is —(CH$_2$)$_{n1}$—NH—C(O)—(CH$_2$)$_{n2}$—CH$_3$, R$^2$ is OH, R$^3$ is H, R$^4$ is H, n1 is 2 and n2 is 10.

* * * * *